US008124057B2

(12) United States Patent
Bosch et al.

(10) Patent No.: US 8,124,057 B2

(45) **Date of Patent: *Feb. 28, 2012**

(54) PROPELLANT-BASED NANOPARTICULATE DRY POWDER AEROSOLS AND METHOD OF MAKING

(75) Inventors: H. William Bosch, Bryn Mawr, PA (US); Kevin D. Ostrander, Reading, PA (US); Eugene R. Cooper, Berwyn, PA (US)

(73) Assignee: Alkermes Pharma Ireland Limited, County Westmeath (IE)

( * ) Notice: Subject to any disclaimer, the term of this patent is extended or adjusted under 35 U.S.C. 154(b) by 88 days.

This patent is subject to a terminal disclaimer.

(21) Appl. No.: 12/320,431

(22) Filed: Jan. 26, 2009

(65) Prior Publication Data

US 2009/0181100 A1 Jul. 16, 2009

Related U.S. Application Data

(63) Continuation of application No. 09/190,138, filed on Nov. 12, 1998, now Pat. No. 7,521,068.

(51) Int. Cl.

| | |
|---|---|
| *A61K 9/00* | (2006.01) |
| *A61K 9/10* | (2006.01) |
| *A61K 9/12* | (2006.01) |

(52) U.S. Cl. ........................................................ 424/45

(58) Field of Classification Search ..................... 424/45

See application file for complete search history.

(56) References Cited

U.S. PATENT DOCUMENTS

| | | | | |
|---|---|---|---|---|
| 3,219,533 | A * | 11/1965 | Mullins | 222/192 |
| 3,269,798 | A | 8/1966 | Preston | |
| 3,692,532 | A | 9/1972 | Shankenberg et al. | |
| 4,389,397 | A | 6/1983 | Lo et al. | |
| 4,540,602 | A | 9/1985 | Motoyama et al. | |
| 4,562,069 | A | 12/1985 | Hegasy et al. | |
| 4,665,081 | A | 5/1987 | Doi et al. | |
| 4,727,077 | A | 2/1988 | Haga et al. | |
| 4,757,059 | A | 7/1988 | Sorenson | |
| 4,765,990 | A | 8/1988 | Sugimoto et al. | |
| 4,807,814 | A | 2/1989 | Douche et al. | |
| 4,826,821 | A | 5/1989 | Clements | |
| 4,851,421 | A | 7/1989 | Iwasaki et al. | |
| 4,880,634 | A | 11/1989 | Speiser | |
| 4,904,668 | A | 2/1990 | Kondo et al. | |
| 4,917,816 | A | 4/1990 | Self | |
| 4,983,605 | A | 1/1991 | Kondo et al. | |
| 5,002,952 | A | 3/1991 | Kondo et al. | |
| 5,049,322 | A | 9/1991 | Devissaguet et al. | |
| 5,091,187 | A | 2/1992 | Haynes | |
| 5,091,188 | A | 2/1992 | Haynes | |
| 5,098,907 | A | 3/1992 | Kondo et al. | |
| 5,118,528 | A | 6/1992 | Fessi et al. | |
| 5,145,684 | A | 9/1992 | Liversidge et al. | |
| 5,202,110 | A | 4/1993 | Dalby et al. | |
| 5,225,183 | A | 7/1993 | Purewal et al. | |
| 5,260,478 | A | 11/1993 | Bacon et al. | |
| 5,264,213 | A | 11/1993 | Shibahara et al. | |
| 5,264,610 | A | 11/1993 | Bacon | |
| 5,298,262 | A | 3/1994 | Na et al. | |
| 5,300,739 | A | 4/1994 | Bittar | |
| 5,318,767 | A | 6/1994 | Liversidge et al. | |
| 5,322,679 | A | 6/1994 | Bacon et al. | |
| 5,338,761 | A | 8/1994 | Nakajima et al. | |
| 5,346,702 | A | 9/1994 | Na et al. | |
| 5,399,363 | A | 3/1995 | Liversidge et al. | |
| 5,466,440 | A | 11/1995 | Ruddy et al. | |
| 5,503,723 | A | 4/1996 | Ruddy et al. | |
| 5,510,118 | A | 4/1996 | Bosch et al. | |
| 5,518,738 | A | 5/1996 | Eickhoff et al. | |
| 5,521,168 | A | 5/1996 | Clark | |
| 5,552,160 | A * | 9/1996 | Liversidge et al. | 424/489 |
| 5,585,108 | A | 12/1996 | Ruddy et al. | |
| 5,595,762 | A | 1/1997 | Derrieu et al. | |
| 5,656,299 | A | 8/1997 | Kino et al. | |
| 5,719,147 | A * | 2/1998 | Dorn et al. | 514/227.5 |
| 5,747,001 | A | 5/1998 | Wiedmann et al. | |
| 5,785,049 | A | 7/1998 | Smith et al. | |
| 5,795,909 | A | 8/1998 | Shashoua et al. | |
| 5,871,747 | A | 2/1999 | Gengoux-Sedilik et al. | |
| 5,904,929 | A | 5/1999 | Uekama et al. | |
| 5,916,596 | A | 6/1999 | Desai et al. | |
| 5,972,389 | A | 10/1999 | Shell et al. | |
| 5,985,309 | A | 11/1999 | Edwards et al. | |
| 6,001,336 | A | 12/1999 | Gordon | |
| 6,004,582 | A | 12/1999 | Faour et al. | |
| 6,017,932 | A | 1/2000 | Singh et al. | |

(Continued)

FOREIGN PATENT DOCUMENTS

| | | |
|---|---|---|
| CA | 2346001 | 4/2000 |

(Continued)

OTHER PUBLICATIONS

Merriam-Webster's Collegiate Dictionary, 10th edition, Merriam-Webster Incorporated: Springfield, Massachusetts, 1993, pp. 311.*

Folke Moren, Chapt. 13, Aerosol Dosage Forms and Formulations, Aerosols in Medicine. Principles, Diagnosis and Therapy (Elsevier Science Publishers 1993).

Soviet Union Abstract No. 628930, "Bulb-Actuated Ejector for Powered Medicinal Substance," (1978).

Matsumoto et al., "Physical Properties of Solid Molecular dispersions of Indomethacin with Poly(vinylpyrrolidone) and Poly(vinylpyrrolidone-co-vinyl-acetate) in Relation to Indomethacin Crystallization," *Pharmaceutical Research* (1999), vol. 16, No. 11, pp. 1722-1728, XP000987250.

Hülsmann et al., "Melt extrusion—an alternative method for enhancing the dissolution rate of 17β-estradiol hemihydrate," *European Journal of Pharmaceutics and Biopharmaceutics* (2000), vol. 49, No. 3, pp. 237-242, XP004257163.

Vojnovic et al., "Formulation and evaluation of vinylpyrrolidone/vinylacetate copolymer microspheres and griseofulvin," *J. Microencapsulation* (1993), vol. 10, No. 1, pp. 89-99, XP000334996.

(Continued)

*Primary Examiner* — James H. Alstrum-Acevedo

(74) *Attorney, Agent, or Firm* — Foley & Lardner LLP

(57) ABSTRACT

There invention discloses aqueous dispersions of nanoparticulate aerosol formulations, dry powder nanoparticulate aerosol formulation, propellant-based aerosol formulations, methods of using the formulations in aerosol delivery devices, and methods of making such formulations. The nanoparticles of the aqueous dispersions or dry powder formulations comprise insoluble drug particles having a surface modifier on the surface thereof.

9 Claims, 16 Drawing Sheets

U.S. PATENT DOCUMENTS

| | | | |
|---|---|---|---|
| 6,045,829 A | 4/2000 | Liversidge et al. |
| 6,068,858 A | 5/2000 | Liversidge et al. |
| 6,177,103 B1 | 1/2001 | Pace et al. |
| 6,177,104 B1 | 1/2001 | Allen et al. |
| 6,193,960 B1 | 2/2001 | Metzger et al. |
| 6,197,349 B1 | 3/2001 | Westesen et al. |
| 6,228,399 B1 | 5/2001 | Parikh et al. |
| 6,303,147 B1 | 10/2001 | Gilis |
| 6,316,029 B1 | 11/2001 | Jain et al. |
| 6,368,620 B2 | 4/2002 | Liu et al. |
| 6,375,986 B1 | 4/2002 | Ryde et al. |
| 6,395,300 B1 | 5/2002 | Straub et al. |
| 6,458,373 B1 | 10/2002 | Lambert et al. |
| 6,592,903 B2 | 7/2003 | Ryde et al. |
| 2002/0002294 A1 | 1/2002 | Cushman |
| 2002/0012675 A1 | 1/2002 | Jain et al. |
| 2002/0055462 A1 | 5/2002 | Reed et al. |
| 2002/0165265 A1 | 11/2002 | Hunter et al. |
| 2003/0077329 A1 | 4/2003 | Kipp et al. |
| 2004/0033267 A1 | 2/2004 | Merisko-Liversidge et al. |
| 2010/0322852 A1 | 12/2010 | Merisko-Liversidge |

FOREIGN PATENT DOCUMENTS

| | | |
|---|---|---|
| DE | 43 27 063 A1 | 2/1995 |
| EP | 0 220 760 A2 | 10/1985 |
| EP | 0 262 560 A2 | 9/1987 |
| EP | 0 347 779 | 12/1989 |
| EP | 0 486 153 A2 | 5/1992 |
| EP | 0 499299 A2 | 8/1992 |
| EP | 0 602 702 A1 | 12/1993 |
| EP | 0 600 532 A2 | 6/1994 |
| EP | 0 601 619 | 6/1994 |
| EP | 0 602 702 A1 | 6/1994 |
| EP | 0 577 215 | 3/2000 |
| EP | 1 010 435 A1 | 6/2000 |
| EP | 1 800 666 A1 | 6/2007 |
| GB | 2 224 258 A | 5/1990 |
| GB | 2 237 510 | 8/1991 |
| GB | 2 316 316 | 2/1998 |
| JP | 57-26615 | 2/1982 |
| JP | 2-167222 | 6/1990 |
| JP | 03/066613 | 3/1991 |
| JP | 4-295420 | 10/1992 |
| JP | 07-112936 | 5/1995 |
| JP | 8-507075 | 7/1996 |
| JP | 8-259460 | 10/1996 |
| JP | 9-241178 | 9/1997 |
| JP | 2004-513886 | 5/2004 |
| WO | WO 90/15593 | 12/1990 |
| WO | WO 91/16038 | 10/1991 |
| WO | WO 92/08446 | 5/1992 |
| WO | 93/13773 | 7/1993 |
| WO | WO 93/25190 | 12/1993 |
| WO | WO 93/25194 | 12/1993 |
| WO | WO 93/25195 | 12/1993 |
| WO | WO 94/18954 | 9/1994 |
| WO | WO 94/20072 | 9/1994 |
| WO | WO 95/05164 | 2/1995 |
| WO | 95/27475 | 10/1995 |
| WO | WO 95/27475 | 10/1995 |
| WO | WO 96/20698 | 7/1996 |
| WO | WO 96/20698 A2 | 7/1996 |
| WO | WO 96/24335 | 8/1996 |
| WO | WO 96/25918 | 8/1996 |
| WO | WO 97/18796 | 5/1997 |
| WO | WO 98/04291 | 2/1998 |
| WO | WO 98/07414 | 2/1998 |
| WO | WO 98/14174 | 4/1998 |
| WO | WO 98/31360 | 7/1998 |
| WO | WO 98/31360 A1 | 7/1998 |
| WO | WO 98/35666 | 8/1998 |
| WO | WO 99/02665 | 1/1999 |
| WO | WO 99/25354 | 5/1999 |
| WO | WO 99/30687 | 6/1999 |
| WO | WO 99/38493 | 8/1999 |
| WO | WO 99/45779 | 9/1999 |
| WO | WO 99/65469 | 12/1999 |
| WO | WO 00/13672 | 3/2000 |
| WO | 00/18374 | 4/2000 |
| WO | WO 00/32189 | 6/2000 |
| WO | WO 00/47196 | 8/2000 |
| WO | WO 00/51572 | 9/2000 |
| WO | WO 0053164 | 9/2000 |
| WO | WO 01/17546 A1 | 3/2001 |
| WO | WO 01/26635 | 4/2001 |
| WO | WO 01/78505 A1 | 10/2001 |
| WO | WO 01/78680 A2 | 10/2001 |
| WO | WO 01/91750 A1 | 12/2001 |
| WO | WO 01/92584 A1 | 12/2001 |
| WO | WO 02/24163 | 3/2002 |
| WO | WO 02/067901 A1 | 9/2002 |
| WO | WO 03/080027 A1 | 10/2003 |
| WO | WO 03/094894 A1 | 11/2003 |
| WO | WO 03/103633 A1 | 12/2003 |

OTHER PUBLICATIONS

Bogdanova et al., "Solid Dispersions of Isopropylantipyrin," *Labo-Pharma-Probl. Tech.* (1984), vol. 32, No. 348, pp. 835-837, XP001097528.

Zingone et al., "Characterization and dissolution study of solid dispersions of theophylline and indomethacin with PVP/VA copolymers," *STP Pharma Sciences* (1992), vol. 2, No. 2, pp. 186-192, XP002111752.

Office Action for related U.S. Appl. No. 12/078,027 dated Dec. 12, 2008.

Office Action for related U.S. Appl. No. 11/898,274 dated Oct. 16, 2008.

Office Action for related U.S. Appl. No. 10/667,470 dated Nov. 12, 2008.

Office Action for related U.S. Appl. No. 11/980,586 dated Sep. 22, 2008.

Office Action for related U.S. Appl. No. 10/712,259 dated Mar. 17, 2008.

Office Action for related U.S. Appl. No. 10/701,064 dated Feb. 7, 2008.

Office Action cited in related U.S. Appl. No. 11/979,231, dated Mar. 16, 2010.

Office Action cited in related U.S. Appl. No. 11/980,720, dated Mar. 29, 2010.

Butler et al., "Effects of Protein Stabilizing Agents on Thermal Backbone Motions: A Disulfide Trapping Study," *Biochemistry*, vol. 35, pp. 10595-10600 (1996).

Office Action cited in related U.S. Appl. No. 09/337,675, dated Feb. 18, 2010.

Canadian Office Action for related Canadian Patent Application No. 2,488,499, dated Feb. 8, 2010.

Office Action cited in related U.S. Appl. No. 10/697,703, dated Feb. 18, 2010.

Office Action dated Feb. 12, 2009 for related U.S. Appl. No. 10/701,064, 12 pgs.

Notice of Reasons for Rejections dated Jan. 6, 2009, for related Japanese Patent Application No. 2001-583733, 5 pgs.

Decision on Rejection cited in related Japanese Patent Application No. 2001-583733, dated Jun. 9, 2010, 3 pgs.

"Design and Evaluation of Oral Administration Drug Formulation", *Pharmaceutical Industry Time Signal Company*, pp. 167-168 (1995).

Office Action dated Mar. 13, 2009 for related U.S. Appl. No. 11/979,231, 15 pgs.

Office Action cited in related U.S. Appl. No. 11/898,274 dated May 5, 2009.

Office Action cited in related U.S. Appl. No. 10/677,857 dated Jul. 8, 2009.

Office Action cited in related U.S. Appl. No. 10/697,703 dated Jul. 9, 2009.

Office Action cited in related U.S. Appl. No. 10/667,470 dated May 19, 2009.

Office Action cited in related U.S. Appl. No. 10/697,716 dated Apr. 15, 2009.

Office Action cited in related U.S. Appl. No. 12/292,395, dated May 26, 2010.

Canadian Office Action dated Jul. 6, 2010 cited in related Canadian Patent Application No. 2,492,488, 3 pgs.
Office Action cited in related U.S. Appl. No. 10/667,470, dated Jul. 27, 2010.
Office Action cited in related U.S. Appl. No. 11/650,412, dated May 12, 2009.
Office Action cited in related U.S. Appl. No. 10/619,539 dated Sep. 8, 2009.
Office Action cited in related U.S. Appl. No. 11/979,231 dated Sep. 16, 2009.
Office Action cited in related U.S. Appl. No. 10/697,716 dated Sep. 15, 2009.
Notice of Reasons for Rejection cited in related Japanese Patent Application No. 2003-565446, dated Jan. 20, 2010, 4 pgs.
Notice of Rejections completed Aug. 24, 2009 for related Japanese Patent Application No. 2002-590934, and Notice of Rejections completed Apr. 24, 2008.
Notice of Rejections completed Aug. 26, 2009 for related Japanese Patent Application No. 2001-583733.
Office Action cited in related U.S. Appl. No. 10/667,470, dated Dec. 29, 2009.
Office Action cited in related U.S. Appl. No. 10/701,064, dated Nov. 23, 2009.
Office Action cited in related U.S. Appl. No. 11/979,240, dated Dec. 16, 2009.
Notice of Reasons for Rejection cited in related Japanese Patent Application No. 2004-510760 dated Dec. 2, 2009, 4 pgs.
Notice of Reasons for Rejection cited in related Japanese Patent Application No. 2004-521891 dated Dec. 22, 2009, 3 pgs.
Edwdards et al., "Large Porous Particles for Pulmonary Drug Delivery," *Science*,276:1868-1871 (Jun. 20, 1997).
"Test Method B527-93(2000)el Standard Test Method for Determination of Tap Density of Metallic Powders and Compounds," www/astm.org/DATABASE.CART/PAGES/B527.htm (2001).
"Autotap and Dual Autotap," www.quantachrome.com/Density/Autotap.htm (2001).
"Optimal Tapped Density Tester," optimalcontrol.com/tapped.html (2001).
European Search Report for related EP Patent Application No. 10179894, dated Nov. 4, 2010.
Office Action cited in related U.S. Appl. No. 10/697,703, dated Nov. 9, 2010.
Office Action cited in related U.S. Appl. No. 11/367,716, dated Nov. 10, 2010.
Office Action cited in related U.S. Appl. No. 12/117,982, dated Dec. 1, 2010.
Office Action cited in related U.S. Appl. No. 12/292,395, dated Dec. 6, 2010.
Office Action cited in related U.S. Appl. No. 11/980,720, dated Dec. 22, 2010.
European Search Report cited in related EP Patent Application No. EP 10 01 0944, dated Dec. 13, 2010.
Canadian Office Action cited in related Canadian Patent Application No. 2,488,499, dated Dec. 16, 2010.
Office Action cited in related U.S. Appl. No. 09/337,675, dated Jan. 11, 2011.
Damascelli et al., Intraarterial Chemotherapy with Polyoxyethylated Castor Oil Free Paclitaxel, Incorporated in Albumin Nanoparticles (ABI-007) Phase I Study of Patients with Squamous Cell Carcinoma of the Head and Neck and Anal Canal: Preliminary Evidence of Clinical Activity; 2001 Cancer, vol. 92, No. 10, pp. 2592-2602.
Office Action cited in related U.S. Appl. No. 11/928,278, dated Dec. 28, 2009.
Office Action cited in related U.S. Appl. No. 11/928,250, dated Dec. 29, 2009.
Office Action cited in related U.S. Appl. No. 11/928,289, dated Dec. 30, 2009.
Notice of Reasons for Rejections cited in related Japanese Patent Application No. 2003-577857, dated Mar. 29, 2010.
Office Action cited in related U.S. Appl. No. 11/928,250, dated Aug. 4, 2010.
Office Action cited in related U.S. Appl. No. 11/928,278, dated Aug. 4, 2010.
Office Action cited in related U.S. Appl. No. 11/928,289, dated Aug. 3, 2010.
Office Action cited in related U.S. Appl. No. 10/667,470, dated Jul. 27, 2010.
Office Action cited in related U.S. Appl. No. 09/337,675, dated Aug. 30, 2010.
Josefsson et al., "Suppression of Type II Collagen-Induced Arthritis by the Endogenous Estrogen Metabolite 2-Methoxyestradiol," *Arthritis & Rheumatism*, vol. 40, Issue 1, pp. 154-163 (1997).
Office Action cited in related U.S. Appl. No. 12/870,722, dated Oct. 7, 2010.
Office Action cited in related U.S. Appl. No. 12/870,745, dated Oct. 7, 2010.
Office Action cited in related U.S. Appl. No. 12/076,247, dated Aug. 5, 2010.
International Search Report for related International Patent Application No. PCT/US2009/036965, completed Jun. 19, 2009.
Written Opinion of the International Searching Authority for related International Patent Application No. PCT/US2009/036965, completed Jun. 19, 2009.
Notice of Rejections for related Japanese Patent Application No. 2003-577857 completed Jul. 6, 2009, 3 pgs.
Canadian Office Action dated Mar. 10, 2010, cited in related Canadian Patent Application No. 2,479,665.
Canadian Office Action cited in related Canadian Patent Application No. 2475092, dated Jan. 11, 2011.
Calvo et al., "Effect of lysozyme on the stability of polyester nanocapsules and nanoparticles: stabilization approaches," *Biomaterials*, vol. 18, No. 19, pp. 1305-1310 (1997). [Abstract].
Tian et al., Structural Stability Effects on Adsorption of Bacteriophage T4 Lysozyme to Colloidal Silica, *J. Colloid. Interface Sci.*, vol. 200, pp. 146-154 (1998). [Abstract].
Office Action cited in related U.S. Appl. No. 12/117,982, dated Feb. 2, 2011.
Office Action cited in related U.S. Appl. No. 10/701,064, dated Feb. 14, 2011.
Office Action cited in related U.S. Appl. No. 10/619,539, dated Mar. 15, 2011.
Office Action cited in related U.S. Appl. No. 12/870,722, dated Mar. 29, 2011.
Office Action cited in related U.S. Appl. No. 12/870,745, dated Apr. 1, 2011.
Office Action cited in related U.S. Appl. No. 11/928,250, dated Apr. 25, 2011.
Office Action cited in related U.S. Appl. No. 11/928,278, dated Apr. 27, 2011.
Office Action cited in related U.S. Appl. No. 11/928,289, dated Apr. 27, 2011.
Office Action cited in related U.S. Appl. No. 10/667,470, dated May 9, 2011.
Office Action cited in related U.S. Appl. No. 11/367,716, dated May 19, 2011.
Office Action cited in related U.S. Appl. No. 11/980,720, dated May 26, 2011.
Office Action cited in related U.S. Appl. No. 10/677,857, dated Jun. 7, 2011.
Office Action cited in related U.S. Appl. No. 12/483,188, dated Jun. 23, 2011.
Office Action cited in related U.S. Appl. No. 12/117,982, dated Jul. 8, 2011.
Office Action cited in related U.S. Appl. No. 12/076,247, dated Apr. 14, 2011.
Purohit et al., Inhibition of Tumor Necrosis Factor a-Stimulated Aromatase Activity by Microtubule-Stabilizing Agents, Pacilitaxel and 2-Methoxyestradiol, *Biochemical and Biophysical Research Communications*, vol. 261, Issue 1, Jul. 22, 1999, pp. 214-217.
Arsenault et al., Taxol Involution of Collagen-Indued Arthritis: Ultrastructural Correlation with the Inhibition of Synovitis and Neovascularization Clinical Immunology and Immunopathology, vol. 86, Issue 3, Mar. 1998, pp. 280-289.
Waldrep et al., "Operating Characteristics of 18 Different Continuous-Flow Jet Nebulizers with Beclomethasone Dipropionate Liposome Aerosol," pp. 11-17 (1994).

Fox et al., "Performance of a Venturi Eductor as a Feeder in a Pneumatic Conveying System," *Powder and Bulk Engineering*, pp. 33-36 (1988).

Tiano, "Functionality Testing Used to Rationally Assess Performance of a Model Respiratory Solution or Suspension in a Nebulizer (Performance Assessment)", vol. 56/12-B of Dissertation Abstracts International, (1995).

Kondo et al., "Improved Oral Absorption of Enteric Coprecipitates of a Poorly Soluble Drug," *J. Pharm. Sciences*, 83(4):566-570 (1994).

Kondo et al., "Improved Oral Absorption of a Poorly Water-Soluble Drug, HO-221, by Wet-Bead Milling Producing Particles in Submicron Region," *Chem, Pharm. Bull.*, 41(4):737-740 (1993).

Kondo, et al, "Pharmacokinetics of a Micronized, Poorly Water Soluble Drug, HO-221, in Experimental Animals," *Biol. Pharm. Bull.*, 16(8):796-800 (1993).

Prodi et al., "Airborne Particles and their Intrapulmonary Deposition," Scientific Foundations of Respiratory Medicine, pp. 545-558 (1981).

Heyder, "Mechanisms of Aerosol Particle Deposition," Lung Mucociliary Clearance, vol. 80: (6) pp. 820-823 (1981).

Newman, "Therapeutic Aerosols," pp. 197-224, (1984).

Serafin, W. Drugs used in the Treatment of Asthma Goodman and Gilman's: The Pharmacological Basis of Therapeutics, McGraw-Hill New York, p. 666, 1996.

Byron, "Aerosol Formulation, Generation, and Delivery Using Nonmetered Systems", pp. 143-151 (1989).

Office Action dated Oct. 23, 2009 for related U.S. Appl. No. 11/898,274.

Office Action dated Oct. 5, 2009 for related U.S. Appl. No. 11/980,720.

* cited by examiner

STATISTICS

| | | |
|---|---|---|
| MEAN SIZE | : | 1.671 |
| STANDARD DEVIATION | : | 1.334 |
| D(4,3) | : | 1.740 |
| D(3,2) | : | 1.602 |
| MODE (LOG SCALE) | : | 1.65 |
| SPECIFIC SURFACE AREA | : | 2.97 sq meter/g |

| %UNDER | SIZE | %UNDER | SIZE | %UNDER | SIZE |
|---|---|---|---|---|---|
| 10% | 1.157 | 90% | 2.432 | | |
| 50% | 1.675 | | | | |

PARAMETERS

| | | |
|---|---|---|
| MATERIAL | : | SDI-NAPROXEN |
| DENSITY | : | 1.26 |
| RUN LENGTH (sec) | : | 123.9 |
| PMT VOLTAGE | : | 1100.0 |
| SUM OF CHANNELS | : | 46211 |
| LOWER SIZE LIMIT | : | 0.10 |
| UPPER SIZE LIMIT | : | 200.00 |
| NOZZLE TYPE | : | 700mm |
| BASELINE OFFSET | : | 0.10 |
| NOISE FILTER | : | 6.00 |
| REGULARIZATION | : | LOW |

| UPPER SIZE | % IN | LOWER SIZE | % UNDER | UPPER SIZE | % IN | LOWER SIZE | % UNDER | UPPER SIZE | % IN | LOWER SIZE | % UNDER |
|---|---|---|---|---|---|---|---|---|---|---|---|
| 180 | 0.0000 | 160 | 100.00 | 100 | 0.0000 | 86.0 | 100.00 | 10.0 | 0.0000 | 8.60 | 100.00 |
| 160 | 0.0000 | 140 | 100.00 | 86.0 | 0.0000 | 74.0 | 100.00 | 8.60 | 0.0000 | 7.40 | 100.00 |
| 140 | 0.0000 | 120 | 100.00 | 74.0 | 0.0000 | 63.0 | 100.00 | 7.40 | 0.0000 | 6.30 | 100.00 |
| 120 | 0.0000 | 100 | 100.00 | 63.0 | 0.0000 | 54.0 | 100.00 | 6.30 | 0.0004 | 5.40 | 100.00 |
| | | | | 54.0 | 0.0000 | 46.0 | 100.00 | 5.40 | 0.0000 | 4.60 | 100.00 |
| | | | | 46.0 | 0.0000 | 40.0 | 100.00 | 4.60 | 0.0000 | 4.00 | 100.00 |
| | | | | 40.0 | 0.0000 | 34.0 | 100.00 | 4.00 | 0.1153 | 3.40 | 99.885 |
| | | | | 34.0 | 0.0000 | 29.0 | 100.00 | 3.40 | 1.7044 | 2.90 | 98.180 |
| | | | | 29.0 | 0.0000 | 25.0 | 100.00 | 2.90 | 6.4095 | 2.50 | 91.771 |
| | | | | 25.0 | 0.0000 | 22.0 | 100.00 | 2.50 | 9.8151 | 2.20 | 81.956 |
| | | | | 22.0 | 0.0000 | 18.0 | 100.00 | 2.20 | 22.597 | 1.80 | 59.359 |
| | | | | 18.0 | 0.0000 | 16.0 | 100.00 | 1.80 | 15.436 | 1.60 | 43.923 |
| | | | | 16.0 | 0.0000 | 14.0 | 100.00 | 1.60 | 16.757 | 1.40 | 27.166 |
| | | | | 14.0 | 0.0000 | 12.0 | 100.00 | 1.40 | 14.681 | 1.20 | 12.484 |
| | | | | 12.0 | 0.0000 | 10.0 | 100.00 | 1.20 | 8.7303 | 1.00 | 3.7540 |

| UPPER SIZE | % IN | LOWER SIZE | % UNDER |
|---|---|---|---|
| 1.00 | 2.4683 | 0.86 | 1.2857 |
| 0.86 | 0.8394 | 0.74 | 0.4463 |
| 0.74 | 0.3050 | 0.63 | 0.1413 |
| 0.63 | 0.1042 | 0.54 | 0.0371 |
| 0.54 | 0.0333 | 0.46 | 0.0038 |
| 0.46 | 0.0036 | 0.40 | 0.0083 |
| 0.40 | 0.0003 | 0.34 | 0.0000 |
| 0.34 | 0.0000 | 0.29 | 0.0000 |
| 0.29 | 0.0000 | 0.25 | 0.0000 |
| 0.25 | 0.0000 | 0.22 | 0.0000 |
| 0.22 | 0.0000 | 0.18 | 0.0000 |
| 0.18 | 0.0000 | 0.16 | 0.0000 |
| 0.16 | 0.0000 | 0.14 | 0.0000 |
| 0.14 | 0.0000 | 0.12 | 0.0000 |
| 0.12 | 0.0000 | 0.10 | 0.0000 |

FIG. 3 con't

Spray Dried Nanoparticulate Naproxen

STATISTICS

| | | |
|---|---|---|
| MEAN SIZE | : | 2.906 |
| STANDARD DEVIATION | : | 1.524 |
| D(4,3) | : | 3.142 |
| D(3,2) | : | 2.632 |
| MODE (LOG SCALE) | : | 3.66 |
| SPECIFIC SURFACE AREA | : | 1.81 sq meter/g |

PARAMETERS

| | | |
|---|---|---|
| MATERIAL | : | SDI-NAPROXEN |
| DENSITY | : | 1.26 |
| RUN LENGTH (sec) | : | 108.9 |
| PMT VOLTAGE | : | 1100.0 |
| SUM OF CHANNELS | : | 13520 |
| LOWER SIZE LIMIT | : | 0.10 |
| UPPER SIZE LIMIT | : | 200.00 |
| NOZZLE TYPE | : | 700mm |
| BASELINE OFFSET | : | 0.10 |
| NOISE FILTER | : | 6.00 |
| REGULARIZATION | : | LOW |

| %UNDER | SIZE | %UNDER | SIZE |
|---|---|---|---|
| 10% | 1.554 | 90% | 4.651 |
| 50% | 3.183 | | |

| UPPER SIZE | % IN | LOWER SIZE | % UNDER |
|---|---|---|---|
| 180 | 0.0000 | 160 | 100.00 |
| 160 | 0.0000 | 140 | 100.00 |
| 140 | 0.0000 | 120 | 100.00 |
| 120 | 0.0000 | 100 | 100.00 |
| 100 | 0.0000 | 86.0 | 100.00 |
| 86.0 | 0.0000 | 74.0 | 100.00 |
| 74.0 | 0.0000 | 63.0 | 100.00 |
| 63.0 | 0.0000 | 54.0 | 100.00 |
| 54.0 | 0.0000 | 46.0 | 100.00 |
| 46.0 | 0.0000 | 40.0 | 100.00 |
| 40.0 | 0.0000 | 34.0 | 100.00 |
| 34.0 | 0.0000 | 29.0 | 100.00 |
| 29.0 | 0.0000 | 25.0 | 100.00 |
| 25.0 | 0.0000 | 22.0 | 100.00 |
| 22.0 | 0.0000 | 18.0 | 100.00 |
| 18.0 | 0.0000 | 16.0 | 100.00 |
| 16.0 | 0.0000 | 14.0 | 100.00 |
| 14.0 | 0.0000 | 12.0 | 100.00 |
| 12.0 | 0.0000 | 10.0 | 100.00 |

| UPPER SIZE | % IN | LOWER SIZE | % UNDER |
|---|---|---|---|
| 10.0 | 0.0000 | 8.60 | 100.00 |
| 8.60 | 0.0000 | 7.40 | 100.00 |
| 7.40 | 0.0000 | 6.30 | 100.00 |
| 6.30 | 1.1614 | 5.40 | 98.839 |
| 5.40 | 9.8645 | 4.60 | 88.974 |
| 4.60 | 13.706 | 4.00 | 75.268 |
| 4.00 | 18.274 | 3.40 | 56.994 |
| 3.40 | 15.715 | 2.90 | 41.278 |
| 2.90 | 10.821 | 2.50 | 30.457 |
| 2.50 | 7.2247 | 2.20 | 23.232 |
| 2.20 | 8.6259 | 1.80 | 14.686 |
| 1.80 | 3.7744 | 1.60 | 10.832 |
| 1.60 | 3.5448 | 1.40 | 7.2871 |
| 1.40 | 3.1759 | 1.20 | 4.1112 |
| 1.20 | 2.4167 | 1.00 | 1.6945 |

| UPPER SIZE | % IN | LOWER SIZE | % UNDER |
|---|---|---|---|
| 1.00 | 1.0101 | 0.86 | 0.6844 |
| 0.86 | 0.4335 | 0.74 | 0.2509 |
| 0.74 | 0.1785 | 0.63 | 0.0723 |
| 0.63 | 0.0548 | 0.54 | 0.0175 |
| 0.54 | 0.0153 | 0.46 | 0.0021 |
| 0.46 | 0.0020 | 0.40 | 0.0001 |
| 0.40 | 0.0001 | 0.34 | 0.0000 |
| 0.34 | 0.0000 | 0.29 | 0.0000 |
| 0.29 | 0.0000 | 0.25 | 0.0000 |
| 0.25 | 0.0000 | 0.22 | 0.0000 |
| 0.22 | 0.0000 | 0.18 | 0.0000 |
| 0.18 | 0.0000 | 0.16 | 0.0000 |
| 0.16 | 0.0000 | 0.14 | 0.0000 |
| 0.14 | 0.0000 | 0.12 | 0.0000 |
| 0.12 | 0.0000 | 0.10 | 0.0000 |

FIG. 5 con't

STATISTICS

| | | |
|---|---|---|
| MEAN SIZE | : | 5.540 |
| STANDARD DEVIATION | : | 1.455 |
| D(4,3) | : | 5.924 |
| D(3,2) | : | 5.146 |
| MODE (LOG SCALE) | : | 4.82 |
| SPECIFIC SURFACE AREA | : | 0.93 sq meter/g |

PARAMETERS

| | | |
|---|---|---|
| MATERIAL | : | SDI-NAPROXEN |
| DENSITY | : | 1.26 |
| RUN LENGTH (sec) | : | 189.6 |
| PMT VOLTAGE | : | 1100.0 |
| SUM OF CHANNELS | : | 100494 |
| LOWER SIZE LIMIT | : | 0.10 |
| UPPER SIZE LIMIT | : | 200.00 |
| NOZZLE TYPE | : | 700mm |
| BASELINE OFFSET | : | 0.10 |
| NOISE FILTER | : | 6.00 |
| REGULARIZATION | : | OFF |

| %UNDER | SIZE | %UNDER | SIZE |
|---|---|---|---|
| 10% | 3.600 | 90% | 9.082 |
| 50% | 5.516 | | |

| UPPER SIZE | % IN | LOWER SIZE | % UNDER | UPPER SIZE | % IN | LOWER SIZE | % UNDER |
|---|---|---|---|---|---|---|---|
| 180 | 0.0000 | 160 | 100.00 | 100 | 0.0000 | 86.0 | 100.00 |
| 160 | 0.0000 | 140 | 100.00 | 86.0 | 0.0000 | 74.0 | 100.00 |
| 140 | 0.0000 | 120 | 100.00 | 74.0 | 0.0000 | 63.0 | 100.00 |
| 120 | 0.0000 | 100 | 100.00 | 63.0 | 0.0000 | 54.0 | 100.00 |
| | | | | 54.0 | 0.0000 | 46.0 | 100.00 |
| | | | | 46.0 | 0.0000 | 40.0 | 100.00 |
| | | | | 40.0 | 0.0000 | 34.0 | 100.00 |
| | | | | 34.0 | 0.0000 | 29.0 | 100.00 |
| | | | | 29.0 | 0.0000 | 25.0 | 100.00 |
| | | | | 25.0 | 0.0000 | 22.0 | 100.00 |
| | | | | 22.0 | 0.0000 | 18.0 | 100.00 |
| | | | | 18.0 | 0.0000 | 16.0 | 100.00 |
| | | | | 16.0 | 0.0000 | 14.0 | 100.00 |
| | | | | 14.0 | 0.0000 | 12.0 | 100.00 |
| | | | | 12.0 | 3.8201 | 10.0 | 94.180 |

| UPPER SIZE | % IN | LOWER SIZE | % UNDER | UPPER SIZE | % IN | LOWER SIZE | % UNDER |
|---|---|---|---|---|---|---|---|
| 10.0 | 7.5026 | 8.60 | 86.677 | 1.00 | 0.0237 | 0.86 | 0.0213 |
| 8.60 | 10.326 | 7.40 | 76.352 | 0.86 | 0.0121 | 0.74 | 0.0092 |
| 7.40 | 13.417 | 6.30 | 62.935 | 0.74 | 0.0064 | 0.63 | 0.0028 |
| 6.30 | 14.999 | 5.40 | 47.935 | 0.63 | 0.0021 | 0.54 | 0.0006 |
| 5.40 | 16.094 | 4.60 | 31.841 | 0.54 | 0.0006 | 0.46 | 0.0001 |
| 4.60 | 13.547 | 4.00 | 18.295 | 0.46 | 0.0001 | 0.40 | 0.0000 |
| 4.00 | 11.255 | 3.40 | 7.0394 | 0.40 | 0.0000 | 0.34 | 0.0000 |
| 3.40 | 3.2799 | 2.90 | 3.7595 | 0.34 | 0.0000 | 0.29 | 0.0000 |
| 2.90 | 1.3355 | 2.50 | 2.4240 | 0.29 | 0.0000 | 0.25 | 0.0000 |
| 2.50 | 0.8131 | 2.20 | 1.6109 | 0.25 | 0.0000 | 0.22 | 0.0000 |
| 2.20 | 0.8995 | 1.80 | 0.7114 | 0.22 | 0.0000 | 0.18 | 0.0000 |
| 1.80 | 0.3128 | 1.60 | 0.3985 | 0.18 | 0.0000 | 0.16 | 0.0000 |
| 1.60 | 0.1861 | 1.40 | 0.2125 | 0.16 | 0.0000 | 0.14 | 0.0000 |
| 1.40 | 0.1061 | 1.20 | 0.1063 | 0.14 | 0.0000 | 0.12 | 0.0000 |
| 1.20 | 0.0613 | 1.00 | 0.0450 | 0.12 | 0.0000 | 0.10 | 0.0000 |

*FIG. 6 con't*

FIGURE 7(A)

Spray-dried nanoparticulate budesonide

FIGURE 7(B)

Micronized budesonide

Micrograph of
Milled TA (3.6%) with Span 85 (0.5%)

FIGURE 12
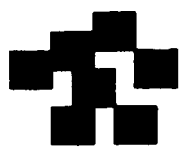
Micronized Drug Substance
not less than 2 μm in diameter
(A)
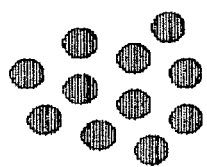
Respirable Aggregates of Nanoparticles
Less than 2 μm to 100 μm in diameter
(B)
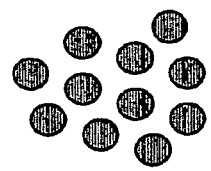
Respirable Diluent Particles Containing
Embedded of Nanoparticles. Less than 2
μm to 100 μm in diameter
(C)

FIGURE 13

Respirable aggregates of nanoparticles mixed with an inert carrier (A)

Respirable diluent particles containing embedded nanoparticles mixed with an inert carrier.

(B)

PROPELLANT-BASED NANOPARTICULATE DRY POWDER AEROSOLS AND METHOD OF MAKING

CROSS-REFERENCE TO RELATED APPLICATION

This application is a continuation of U.S. patent application Ser. No. 09/190,138, filed on Nov. 12, 1998 now U.S. Pat. No. 7,521,068. The contents of that application is hereby incorporated by reference in its entirety.

FIELD OF THE INVENTION

The present invention is directed to aerosol formulations of nanoparticulate drug compositions, and methods of making and using such aerosol formulations.

BACKGROUND OF THE INVENTION

The route of administration of a drug substance can be critical to its pharmacological effectiveness. Various routes of administration exist, and all have their own advantages and disadvantages. Oral drug delivery of tablets, capsules, liquids, and the like is the most convenient approach to drug delivery, but many drug compounds are not amenable to oral administration. For example, modern protein drugs which are unstable in the acidic gastric environment or which are rapidly degraded by proteolytic enzymes in the digestive tract are poor candidates for oral administration. Similarly, poorly soluble compounds which do not dissolve rapidly enough to be orally absorbed are likely to be ineffective when given as oral dosage forms. Oral administration can also be undesirable because drugs which are administered orally are generally distributed to all tissues in the body, and not just to the intended site of pharmacological activity. Alternative types of systemic administration are subcutaneous or intravenous injection. This approach avoids the gastrointestinal tract and therefore can be an effective route for delivery of proteins and peptides. However, these routes of administration have a low rate of patient compliance, especially for drugs such as insulin which must be administered one or more times daily. Additional alternative methods of drug delivery have been developed including transdermal, rectal, vaginal, intranasal, and pulmonary delivery.

Nasal drug delivery relies on inhalation of an aerosol through the nose so that active drug substance can reach the nasal mucosa. Drugs intended for systemic activity can be absorbed into the bloodstream because the nasal mucosa is highly vascularized. Alternatively, if the drug is intended to act topically, it is delivered directly to the site of activity and does not have to distribute throughout the body; hence, relatively low doses may be used. Examples of such drugs are decongestants, antihistamines, and anti-inflammatory steroids for seasonal allergic rhinitis.

Pulmonary drug delivery relies on inhalation of an aerosol through the mouth and throat so that the drug substance can reach the lung. For systemically active drugs, it is desirable for the drug particles to reach the alveolar region of the lung, whereas drugs which act on the smooth muscle of the conducting airways should preferentially deposit in the bronchiole region. Such drugs can include beta-agonists, anticholinergics, and corticosteroids.

Devices Used for Nasal and Pulmonary Drug Delivery

Drugs intended for intranasal delivery (systemic and local) can be administered as aqueous solutions or suspensions, as solutions or suspensions in halogenated hydrocarbon propellants (pressurized metered-dose inhalers), or as dry powders. Metered-dose spray pumps for aqueous formulations, pMDIs, and DPIs for nasal delivery, are available from, for example, Valois of America or Pfeiffer of America.

Drugs intended for pulmonary delivery can also be administered as aqueous formulations, as suspensions or solutions in halogenated hydrocarbon propellants, or as dry powders. Aqueous formulations must be aerosolized by liquid nebulizers employing either hydraulic or ultrasonic atomization, propellant-based systems require suitable pressurized metered-dose inhalers (pMDIs), and dry powders require dry powder inhaler devices (DPIs) which are capable of dispersing the drug substance effectively. For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Heathcare, Inc. and DeVilbiss Health Care, Inc.

A propellant driven inhaler (PMDI) releases a metered dose of medicine upon each actuation. The medicine is formulated as a suspension or solution of a drug substance in a suitable propellant such as a halogenated hydrocarbon. pMDIs are described in, for example, Newman, S. P., *Aerosols and the Lung*, Clarke et al., eds., pp. 197-224 (Butterworths, London, England, 1984).

Dry powder inhalers (DPIs), which involve deaggregation and aerosolization of dry powders, normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage; SU 628930 (Abstract), describing a hand-held powder disperser having an axial air flow tube; Fox et al., *Powder and Bulk Engineering*, pages 33-36 (March 1988), describing a venturi eductor having an axial air inlet tube upstream of a venturi restriction; EP 347 779, describing a hand-held powder disperser having a collapsible expansion chamber; and U.S. Pat. No. 5,785,049, directed to dry powder delivery devices for drugs.

Droplet/Particle Size Determines Deposition Site

In developing a therapeutic aerosol, the aerodynamic size distribution of the inhaled particles is the single most important variable in defining the site of droplet or particle deposition in the patient; in short, it will determine whether drug targeting succeeds or fails. See P. Byron, "Aerosol Formulation, Generation, and Delivery Using Nonmetered Systems," *Respiratory Drug Delivery*, 144-151, 144 (CRC Press, 1989). Thus, a prerequisite in developing a therapeutic aerosol is a preferential particle size. The deposition of inhaled aerosols involves different mechanisms for different size particles. D. Swift (1980); Parodi et al., "Airborne Particles and Their Pulmonary Deposition," in *Scientific Foundations of Respiratory Medicine*, Scaddings et al. (eds.), pp. 545-557 (W.B. Saunders, Philadelphia, 1981); J. Heyder, "Mechanism of Aerosol Particle Deposition," *Chest*, 80:820-823 (1981).

Generally, inhaled particles are subject to deposition by one of two mechanisms: impaction, which usually predominates for larger particles, and sedimentation, which is prevalent for smaller particles. Impaction occurs when the momentum of an inhaled particle is large enough that the particle does not follow the air stream and encounters a physiological surface. In contrast, sedimentation occurs primarily in the deep lung when very small particles which have traveled with the inhaled air stream encounter physiological surfaces as a result of random diffusion within the air stream. For intranasally administered drug compounds which are inhaled through the nose, it is desirable for the drug to impact directly on the nasal mucosa; thus, large (ca. 5 to 100 µm) particles or droplets are generally preferred for targeting of nasal delivery.

Pulmonary drug delivery is accomplished by inhalation of an aerosol through the mouth and throat. Particles having aerodynamic diameters of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Even smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

Problems with Conventional Aerosol Compositions and Methods

Conventional techniques are extremely inefficient in delivering agents to the lung for a variety of reasons. Prior to the present invention, attempts to develop respirable aqueous suspensions of poorly soluble drugs have been largely unsuccessful. For example, it has been reported that ultrasonic nebulization of a suspension containing fluorescein and latex drug spheres, representing insoluble drug particles, resulted in only 1% aerosolization of the particles, while air-jet nebulization resulted in only a fraction of particles being aerosolized. Susan L. Tiano, "Functionality Testing Used to Rationally Assess Performance of a Model Respiratory Solution or Suspension in a Nebulizer," Dissertation Abstracts International, 56/12-B, pp. 6578 (1995). Another problem encountered with nebulization of liquid formulations prior to the present invention was the long (4-20 min) period of time required for administration of a therapeutic dose. Long administration times are required because conventional liquid formulations for nebulization are very dilute solutions or suspensions of micronized drug substance. Prolonged administration times are undesirable because they lessen patient compliance and make it difficult to control the dose administered. Lastly, aerosol formulations of micronized drug are not feasible for deep lung delivery of insoluble compounds because the droplets needed to reach the alveolar region (0.5 to 2 microns) are too small to accommodate micronized drug crystals, which are typically 2-3 microns or more in diameter.

Conventional pMDIs are also inefficient in delivering drug substance to the lung. In most cases, pMDIs consist of suspensions of micronized drug substance in halogenated hydrocarbons such as chlorofluorocarbons (CFCs) or hydrofluoroalkanes (HFAs). Actuation of the pMDI results in delivery of a metered dose of drug and propellant, both of which exit the device at high velocities because of the propellant pressures. The high velocity and momentum of the drug particles results in a high degree of oropharyngeal impaction as well as loss to the device used to deliver the agent. These losses lead to variability in therapeutic agent levels and poor therapeutic control. In addition, oropharyngeal deposition of drugs intended for topical administration to the conducting airways (such as corticosteroids) can lead to systemic absorption with resultant undesirable side effects. Additionally, conventional micronization (air-jet milling) of pure drug substance can reduce the drug particle size to no less than about 2-3 microns. Thus, the micronized material typically used in pMDIs is inherently unsuitable for delivery to the alveolar region and is not expected to deposit below the central bronchiole region of the lung.

Prior to the present invention, delivery of dry powders to the lung typically used micronized drug substance. In the dry powder form, micronized substances tend to have substantial interparticle electrostatic attractive forces which prevent the powders from flowing smoothly and generally make them difficult to disperse. Thus, two key challenges to pulmonary delivery of dry powders are the ability of the device to accurately meter the intended dose and the ability of the device to fully disperse the micronized particles. For many devices and formulations, the extent of dispersion is dependent upon the patient's inspiration rate, which itself may be variable and can lead to a variability in the delivered dose.

Delivery of drugs to the nasal mucosa can also be accomplished with aqueous, propellant-based, or dry powder formulations. However, absorption of poorly soluble drugs can be problematic because of mucociliary clearance which transports deposited particles from the nasal mucosa to the throat where they are swallowed. Complete clearance generally occurs within about 15-20 minutes. Thus, poorly soluble drugs which do not dissolve within this time frame are unavailable for either local or systemic activity.

The development of aerosol drug delivery systems has been hampered by the inherent instability of aerosols, the difficulty of formulating dry powder and aqueous aerosols of water-insoluble drugs, and the difficulty of designing an optimal drug particle size for an aerosol drug delivery system. There is a need in the art for aerosols that deliver an optimal dosage of essentially insoluble drugs throughout the respiratory tract or nasal cavity. The present invention satisfies these needs.

SUMMARY OF THE INVENTION

The present invention is directed to aqueous, propellant-based, and dry powder aerosols of nanoparticulate compositions, for pulmonary and nasal delivery, in which essentially every inhaled particle contains at least one nanoparticulate drug particle. The drug is highly water-insoluble. Preferably, the nanoparticulate drug has an effective average particle size of about 1 micron or less. This invention is an improvement of the nanoparticulate aerosol formulations described in pending U.S. application Ser. No. 08/984,216, filed on Oct. 9, 1997, for "Aerosols Containing Nanoparticulate Dispersions," specifically incorporated by reference. Non-aerosol preparations of submicron sized water-insoluble drugs are described in U.S. Pat. No. 5,145,684, specifically incorporated herein by reference.

A. Aqueous Aerosol Formulations

The present invention encompasses aqueous formulations containing nanoparticulate drug particles. For aqueous aerosol formulations, the drug may be present at a concentration of about 0.05 mg/mL up to about 600 mg/mL. Such formulations provide effective delivery to appropriate areas of the lung or nasal cavities. In addition, the more concentrated aerosol formulations (i.e., for aqueous aerosol formulations, about 10 mg/mL up to about 600 mg/mL) have the additional advantage of enabling large quantities of drug substance to be delivered to the lung in a very short period of time, e.g., about 1 to about 2 seconds (1 puff) as compared to the conventional 4-20 min. administration period.

B. Dry Powder Aerosol Formulations Another embodiment of the invention is directed to dry powder aerosol formulations comprising drug particles for pulmonary and nasal administration. Dry powders, which can be used in both DPIs and pMDIs, can be made by spray-drying aqueous nanoparticulate drug dispersions. Alternatively, dry powders containing nanoparticulate drug can be made by freeze-drying nanoparticulate drug dispersions. Combinations of spray-dried and freeze-dried nanoparticulate drug powders can be used in DPIs and pMDIs. For dry powder aerosol formulations, the drug may be present at a concentration of about 0.05 mg/g up to about 990 mg/g. In addition, the more concentrated aerosol formulations (i.e., for dry powder aerosol formulations about 10 mg/g up to about 990 mg/g) have the additional advantage of enabling large quantities of drug substance to be delivered to the lung in a very short period of time, e.g., about 1 to about 2 seconds (1 puff).

1. Spray-Dried Powders Containing Nanoparticulate Drug

Powders comprising nanoparticulate drug can be made by spray-drying aqueous dispersions of a nanoparticulate drug and a surface modifier to form a dry powder which consists of aggregated drug nanoparticles. The aggregates can have a size of about 1 to about 2 microns which is suitable for deep lung delivery. The aggregate particle size can be increased to target alternative delivery sites, such as the upper bronchial region or nasal mucosa by increasing the concentration of drug in the spray-dried dispersion or by increasing the droplet size generated by the spray dryer.

Alternatively, the aqueous dispersion of drug and surface modifier can contain a dissolved diluent such as lactose or mannitol which, when spray dried, forms respirable diluent particles, each of which contains at least one embedded drug nanoparticle and surface modifier. The diluent particles with embedded drug can have a particle size of about 1 to about 2 microns, suitable for deep lung delivery. In addition, the diluent particle size can be increased to target alternate delivery sites, such as the upper bronchial region or nasal mucosa by increasing the concentration of dissolved diluent in the aqueous dispersion prior to spray drying, or by increasing the droplet size generated by the spray dryer.

Spray-dried powders can be used in DPIs or pMDIs, either alone or combined with freeze-dried nanoparticulate powder. In addition, spray-dried powders containing drug nanoparticles can be reconstituted and used in either jet or ultrasonic nebulizers to generate aqueous dispersions having respirable droplet sizes, where each droplet contains at least one drug nanoparticle. Concentrated nanoparticulate dispersions may also be used in these aspects of the invention.

2. Freeze-Dried Powders Containing Nanoparticulate Drug

Nanoparticulate drug dispersions can also be freeze-dried to obtain powders suitable for nasal or pulmonary delivery. Such powders may contain aggregated nanoparticulate drug particles having a surface modifier. Such aggregates may have sizes within a respirable range, i.e., about 2 to about 5 microns. Larger aggregate particle sizes can be obtained for targeting alternate delivery sites, such as the nasal mucosa.

Freeze dried powders of the appropriate particle size can also be obtained by freeze drying aqueous dispersions of drug and surface modifier, which additionally contain a dissolved diluent such as lactose or mannitol. In these instances the freeze dried powders consist of respirable particles of diluent, each of which contains at least one embedded drug nanoparticle.

Freeze-dried powders can be used in DPIs or pMDIs, either alone or combined with spray-dried nanoparticulate powder. In addition, freeze-dried powders containing drug nanoparticles can be reconstituted and used in either jet or ultrasonic nebulizers to generate aqueous dispersions having respirable droplet sizes, where each droplet contains at least one drug nanoparticle. Concentrated nanoparticulate dispersions may also be used in these aspects of the invention.

C. Propellant-Based Formulations

Yet another embodiment of the invention is directed to a process and composition for propellant-based systems comprising nanoparticulate drug particles and a surface modifier. Such formulations may be prepared by wet milling the coarse drug substance and surface modifier in liquid propellant, either at ambient pressure or under high pressure conditions. Alternatively, dry powders containing drug nanoparticles may be prepared by spray-drying or freeze-drying aqueous dispersions of drug nanoparticles and the resultant powders dispersed into suitable propellants for use in conventional pMDIs. Such nanoparticulate pMDI formulations can be used for either nasal or pulmonary delivery. For pulmonary administration, such formulations afford increased delivery to the deep lung regions because of the small (i.e., about 1 to about 2 microns) particle sizes available from these methods. Concentrated aerosol formulations can also be employed in pMDIs.

D. Methods of Making Aerosol Formulations

The invention also provides methods for making an aerosol of nanoparticulate compositions. The nanoparticulate dispersions used in making aqueous aerosol compositions can be made by wet milling or by precipitation methods known in the art. Dry powders containing drug nanoparticles can be made by spray drying or freeze-drying aqueous dispersions of drug nanoparticles. The dispersions used in these systems may or may not contain dissolved diluent material prior to drying. Additionally, both pressurized and non-pressurized milling operations can be employed to make nanoparticulate drug compositions in non-aqueous systems.

In a non-aqueous, non-pressurized milling system, a non-aqueous liquid which has a vapor pressure of 1 atm or less at room temperature is used as a milling medium and may be evaporated to yield dry nanoparticulate drug and surface modifier. The non-aqueous liquid may be, for example, a high-boiling halogenated hydrocarbon. The dry nanoparticulate drug composition thus produced may then be mixed with a suitable propellant or propellants and used in a conventional pMDI.

Alternatively, in a pressurized milling operation, a non-aqueous liquid which has a vapor pressure>1 atm at room temperature is used as a milling medium for making a nanoparticulate drug and surface modifier composition. Such a liquid may be, for example, a halogenated hydrocarbon propellant which has a low boiling point. The resultant nanoparticulate composition can then be used in a conventional pMDI without further modification, or can be blended with other suitable propellants. Concentrated aerosols may also be made via such methods.

E. Methods of Using Nanoparticulate Aerosol Formulations

In yet another aspect of the invention, there is provided a method of treating a mammal comprising: (1) forming an aerosol of a dispersion (either aqueous or powder) of nanoparticles, wherein the nanoparticles comprise an insoluble drug having a surface modifier on the surface thereof, and (2) administering the aerosol to the pulmonary or nasal cavities of the mammal. Concentrated aerosol formulations may also be used in such methods.

Another embodiment of the invention provides a method of diagnosing a mammal comprising: (1) forming an aerosol of a dispersion (either aqueous or dry) of nanoparticles, wherein the nanoparticles comprise an insoluble diagnostic agent having a surface modifier; (2) administering the aerosol to the pulmonary or nasal cavities of the mammal; and (3) imaging the diagnostic agent in the pulmonary or nasal system. Concentrated aerosol formulations can also be employed in such diagnostic methods.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 7: Shows two photomicrographs: FIG. 7(A) shows spray-dried nanoparticulate budesonide particles, and FIG. 7(B) shows particles of micronized budesonide.

FIG. 11(A) shows aqueous suspension of micronized Drug Substance, and FIG. 11(B) shows colloidal Dispersion of drug nanoparticles.

FIG. 12: FIG. 12(A) shows micronized drug substance not less than 2 μm in diameter, FIG. 12(B) shows respirable aggregates of nanoparticles less than 2 μm to 100 μm in diameter, and FIG. 12(C) shows respirable diluent particles containing embedded of nanoparticles, less than 2 μm to 100 μm in diameter.

FIG. 13: FIG. 13(A) shows respirable aggregates of nanoparticles mixed with an inert carrier, and FIG. 13(B) shows respirable diluent particles containing embedded nanoparticles mixed with an inert carrier.

DETAILED DESCRIPTION OF THE INVENTION

A. Aerosol Formulations

Figure 1:
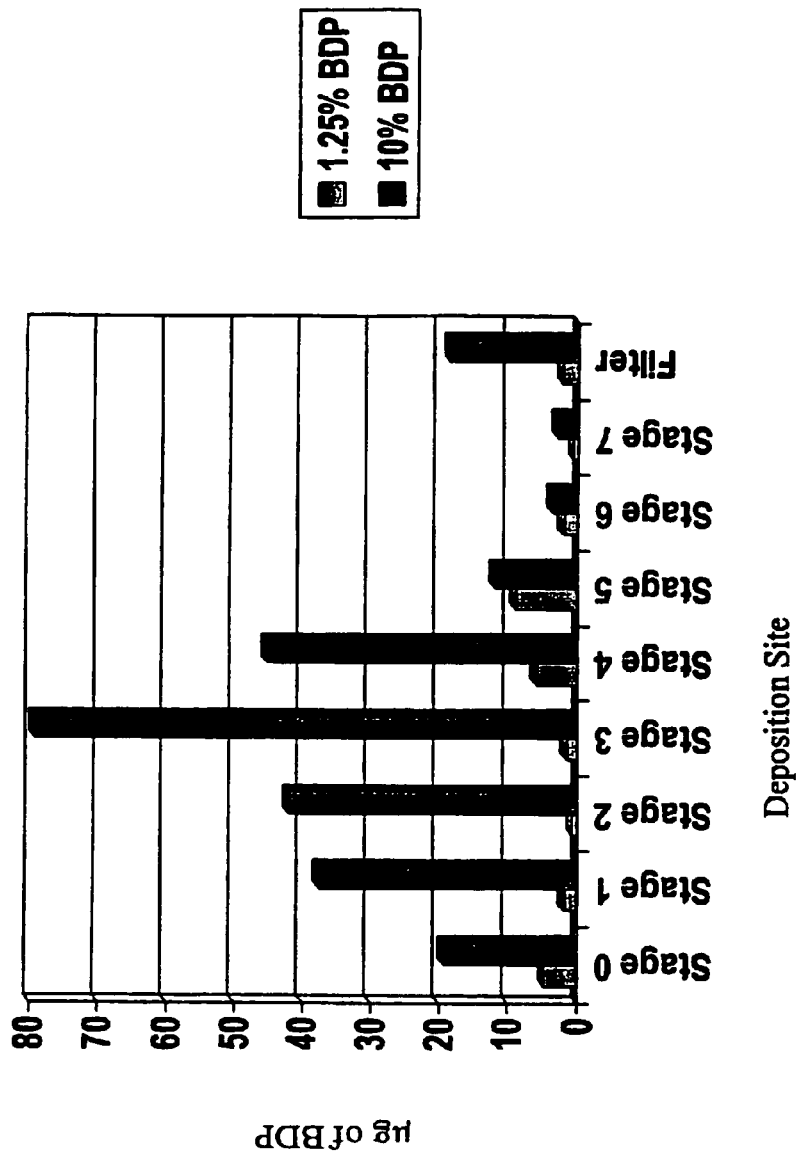
FIG. 1: Shows an in vitro deposition pattern of a concentrated aerosolized beclomethasone dipropionate dispersion from an ultrasonic nebulizer.

The compositions of the invention are aerosols which contain drug nanoparticles. Aerosols can be defined as colloidal systems consisting of very finely divided liquid droplets or dry particles dispersed in and surrounded by a gas. Both liquid and dry powder aerosol compositions are encompassed by the invention.

1. Nanoparticulate Drug and Surface Modifier Particle Size

Preferably, the compositions of the invention contain nanoparticles which have an effective average particle size of less than about 1000 nm, more preferably less than about 400 nm, less than about 300 nm, less than about 250 nm, less than about 100 nm, or less than about 50 nm, as measured by light-scattering methods. By "an effective average particle size of less than about 1000 nm" it is meant that at least 50% of the drug particles have a weight average particle size of less than about 1000 nm when measured by light scattering techniques. Preferably, at least 70% of the drug particles have an average particle size of less than about 1000 nm, more preferably at least 90% of the drug particles have an average particle size of less than about 1000 nm, and even more preferably at least about 95% of the particles have a weight average particle size of less than about 1000 nm.

2. Concentration of Nanoparticulate Drug

For aqueous aerosol formulations, the nanoparticulate agent is present at a concentration of about 0.05 mg/mL up to about 600 mg/mL. For dry powder aerosol formulations, the nanoparticulate agent is present at a concentration of about 0.05 mg/g up to about 990 mg/g, depending on the desired drug dosage. Concentrated nanoparticulate aerosols, defined as containing a nanoparticulate drug at a concentration of about 10 mg/mL up to about 600 mg/mL for aqueous aerosol formulations, and about 10 mg/g up to about 990 mg/g for dry powder aerosol formulations, are specifically encompassed by the present invention. Such formulations provide effective delivery to appropriate areas of the lung or nasal cavities in short administration times, i.e., less than about 15 seconds as compared to administration times of up to 4 to 20 minutes as found in conventional pulmonary nebulizer therapies.

3. In Vivo Deposition of Inhaled Aerosols

Aerosols intended for delivery to the nasal mucosa are inhaled through the nose. For optimal delivery to the nasal cavities, inhaled particle sizes of about 5 to about 100 microns are useful, with particle sizes of about 30 to about 60 microns being preferred. For nasal delivery, a larger inhaled particle size is desired to maximize impaction on the nasal mucosa and to minimize or prevent pulmonary deposition of the administered formulation. Inhaled particles may be defined as liquid droplets containing dissolved drug, liquid droplets containing suspended drug particles (in cases where the drug is insoluble in the suspending medium), dry particles of pure drug substance, aggregates of drug nanoparticles, or dry particles of a diluent which contain embedded drug nanoparticles.

For delivery to the upper respiratory region, inhaled particle sizes of about 2 to about 10 microns are preferred, more preferred is about 2 to about 6 microns. Delivery to the upper respiratory region may be desirable for drugs such as bronchodilators or corticosteroids that are to act locally. This is because drug particles deposited in the upper respiratory tract can dissolve and act on the smooth muscle of the airway, rather than being absorbed into the bloodstream of the patient. However, the goal for some inhaled drugs is systemic delivery, such as in cases of proteins or peptides which are not amenable to oral administration. It is preferred that drugs intended for systemic administration be delivered to the alveolar region of the lung, because 99.99% of the available surface area for drug absorption is located in the peripheral alveoli. Thus, with administration to the alveolar region, rapid absorption can be realized. For delivery to the deep lung (alveolar) region, inhaled particle sizes of less than about 2 microns are preferred.

4. Aqueous Aerosols

Aqueous formulations of the present invention consist of colloidal dispersions of water-insoluble nanoparticulate drug in an aqueous vehicle which are aerosolized using air-jet or ultrasonic nebulizers. The advantages of the present invention can best be understood by comparing the sizes of nanoparticulate and conventional micronized drug particles with the sizes of liquid droplets produced by conventional nebulizers. Conventional micronized material is generally about 2 to about 5 microns or more in diameter and is approximately the same size as the liquid droplet size produced by medical nebulizers. In contrast, nanoparticulate drug particles are substantially smaller than the droplets in such an aerosol. Thus, aerosols containing nanoparticulate drug particles improve drug delivery efficiency because they contain a higher number of drug particles per unit dose such that each aerosolized droplet contains active drug substance.

Thus, with administration of the same dosages of nanoparticulate and micronized drug, more lung or nasal cavity surface area is covered by the aerosol formulation containing nanoparticulate drug.

Another advantage of the present invention is that it permits water-insoluble drug compounds to be delivered to the deep lung via nebulization of aqueous formulations. Conventional micronized drug substance is too large to reach the peripheral lung regardless of the size of the droplet produced by the nebulizer, but the present invention permits nebulizers which generate very small (about 0.5 to about 2 microns) aqueous droplets to deliver water-insoluble drugs in the form of nanoparticles to the alveoli. One example of such devices is the Circulaire® (Westmed Corp., Tucson, Ariz.).

Yet another advantage of the present invention is that ultrasonic nebulizers can be used to deliver water-insoluble drugs to the lung. Unlike conventional micronized material, nanoparticulate drug particles are readily aerosolized and show good in vitro deposition characteristics. A specific advantage of the present invention is that it permits water-insoluble drugs to be aerosolized by ultrasonic nebulizers which require the drug substance to pass through very fine orifices to control the size of the aerosolized droplets. While conventional drug material would be expected to occlude the pores, nanoparticulate drug particles are much smaller and can pass through the pores without difficulty.

Another advantage of the present invention is the enhanced rate of dissolution of water-insoluble drugs. Since dissolution rate is a function of the total surface area of drug substance to be dissolved, more finely divided drug particles (e.g., nanoparticles) have much faster dissolution rates than conventional micronized drug particles. This can result in more rapid absorption of inhaled drugs. For nasally administered drugs it can result in more complete absorption of the dose, since with a nanoparticulate drug dose the particles can dissolve rapidly and completely before being cleared via the mucociliary mechanism.

5. Dry Powder Aerosol Formulations

The invention is also directed to dry powders which contain nanoparticulate compositions for pulmonary or nasal delivery. The powders may consist of respirable aggregates of nanoparticulate drug particles, or of respirable particles of a diluent which contains at least one embedded drug nanoparticle. Powders containing nanoparticulate drug particles can be prepared from aqueous dispersions of nanoparticles by removing the water via spray-drying or lyophilization (freeze drying). Spray-drying is less time consuming and less expensive than freeze-drying, and therefore more cost-effective. However, certain drugs, such as biologicals benefit from lyophilization rather than spray-drying in making dry powder formulations.

Dry powder aerosol delivery devices must be able to accurately, precisely, and repeatably deliver the intended amount of drug. Moreover, such devices must be able to fully disperse the dry powder into individual particles of a respirable size. Conventional micronized drug particles of 2-3 microns in diameter are often difficult to meter and disperse in small quantities because of the electrostatic cohesive forces inherent in such powders. These difficulties can lead to loss of drug substance to the delivery device as well as incomplete powder dispersion and sub-optimal delivery to the lung. Many drug compounds, particularly proteins and peptides, are intended for deep lung delivery and systemic absorption. Since the average particle sizes of conventionally prepared dry powders are usually in the range of 2-3 microns, the fraction of material which actually reaches the alveolar region may be quite small. Thus, delivery of micronized dry powders to the lung, especially the alveolar region, is generally very inefficient because of the properties of the powders themselves.

The dry powder aerosols which contain nanoparticulate drugs can be made smaller than comparable micronized drug substance and, therefore, are appropriate for efficient delivery to the deep lung. Moreover, aggregates of nanoparticulate drugs are spherical in geometry and have good flow properties, thereby aiding in dose metering and deposition of the administered composition in the lung or nasal cavities.

Dry nanoparticulate compositions can be used in both DPIs and pMDIs. (In this invention, "dry" refers to a composition having less than about 5% water.)

6. Propellant-Based Aerosols

Another embodiment of the invention is directed to a process and composition for propellant-based MDIs containing nanoparticulate drug particles. pMDIs can comprise either discrete nanoparticles of drug and surface modifier, aggregates of nanoparticles of drug and surface modifier, or inactive diluent particles containing embedded nanoparticles. pMDIs can be used for targeting the nasal cavity, the conducting airways of the lung, or the alveoli. Compared to conventional formulations, the present invention affords increased delivery to the deep lung regions because the inhaled nanoparticulate drug particles are smaller than conventional micronized material (<2 μm) and are distributed over a larger mucosal or alveolar surface area as compared to micronized drugs.

Nanoparticulate drug pMDIs of the present invention can utilize either chlorinated or non-chlorinated propellants. Concentrated nanoparticulate aerosol formulations can also be employed in pMDIs.

B. Methods of Making Aerosol Formulations

The nanoparticulate drug compositions for aerosol administration can be made by, for example, (1) nebulizing an aqueous dispersion of nanoparticulate drug, obtained by either grinding or precipitation; (2) aerosolizing a dry powder of aggregates of nanoparticulate drug and surface modifier (the aerosolized composition may additionally contain a diluent); or (3) aerosolizing a suspension of nanoparticulate drug or drug aggregates in a non-aqueous propellant. The aggregates of nanoparticulate drug and surface modifier, which may additionally contain a diluent, can be made in a non-pressurized or a pressurized non-aqueous system. Concentrated aerosol formulations may also be made via such methods.

1. Aqueous Milling to Obtain Nanoparticulate Drug Dispersions

Milling of aqueous drug to obtain nanoparticulate drug is described in the '684 patent. In sum, drug particles are dispersed in a liquid dispersion medium and mechanical means is applied in the presence of grinding media to reduce the particle size of the drug to the desired effective average particle size. The particles can be reduced in size in the presence of one or more surface modifiers. Alternatively, the particles can be contacted with one or more surface modifiers after attrition. Other compounds, such as a diluent, can be added to the drug/surface modifier composition during the size reduction process. Dispersions can be manufactured continuously or in a batch mode.

2. Precipitation to Obtain Nanoparticulate Drug Compositions

Another method of forming the desired nanoparticle dispersion is by microprecipitation. This is a method of preparing stable dispersions of drugs in the presence of one or more surface modifiers and one or more colloid stability enhancing surface active agents free of any trace toxic solvents or solubilized heavy metal impurities. Such a method comprises, for example, (1) dissolving the drug in a suitable solvent with mixing; (2) adding the formulation from step (1) with mixing to a solution comprising at least one surface modifier to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate drug dispersion can be utilized in liquid nebulizers or processed to form a dry powder for use in a DPI or pMDI.

3. Non-Aqueous Non-Pressurized Milling Systems

In a non-aqueous, non-pressurized milling system, a non-aqueous liquid having a vapor pressure of about 1 atm or less at room temperature and in which the drug substance is essentially insoluble is used as a wet milling medium to make a nanoparticulate drug composition. In such a process, a slurry of drug and surface modifier is milled in the nonaqueous medium to generate nanoparticulate drug particles. Examples of suitable non-aqueous media include ethanol, trichloromonofluoromethane (CFC-11), and dichlorotetrafluoroethane (CFC-114). An advantage of using CFC-11 is that it can be handled at only marginally cool room temperatures, whereas CFC-114 requires more controlled conditions to avoid evaporation. Upon completion of milling the liquid medium may be removed and recovered under vacuum or heating, resulting in a dry nanoparticulate composition. The dry composition may then be filled into a suitable container and charged with a final propellant. Exemplary final product propellants, which ideally do not contain chlorinated hydrocarbons, include HFA-134a (tetrafluoroethane) and HFA-227 (heptafluoropropane). While non-chlorinated propellants may be preferred for environmental reasons, chlorinated propellants may also be used in this aspect of the invention.

4. Non-Aqueous Pressurized Milling System

In a non-aqueous, pressurized milling system, a non-aqueous liquid medium having a vapor pressure significantly greater than 1 atm at room temperature is used in the milling process to make nanoparticulate drug compositions. If the milling medium is a suitable halogenated hydrocarbon propellant, the resultant dispersion may be filled directly into a suitable pMDI container. Alternately, the milling medium can be removed and recovered under vacuum or heating to yield a dry nanoparticulate composition. This composition can then be filled into an appropriate container and charged with a suitable propellant for use in a pMDI.

5. Spray-Dried Powder Aerosol Formulations

Spray drying is a process used to obtain a powder containing nanoparticulate drug particles following particle size reduction of the drug in a liquid medium. In general, spray-drying is used when the liquid medium has a vapor pressure of less than about 1 atm at room temperature. A spray-dryer is a device which allows for liquid evaporation and drug powder collection. A liquid sample, either a solution or suspension, is fed into a spray nozzle. The nozzle generates droplets of the sample within a range of about 20 to about 100 μm in diameter which are then transported by a carrier gas into a drying chamber. The carrier gas temperature is typically between about 80 and about 200° C. The droplets are subjected to rapid liquid evaporation, leaving behind dry particles which are collected in a special reservoir beneath a cyclone apparatus.

If the liquid sample consists of an aqueous dispersion of nanoparticles and surface modifier, the collected product will consist of spherical aggregates of the nanoparticulate drug particles. If the liquid sample consists of an aqueous dispersion of nanoparticles in which an inert diluent material was dissolved (such as lactose or mannitol), the collected product will consist of diluent (e.g., lactose or mannitol) particles which contain embedded nanoparticulate drug particles. The final size of the collected product can be controlled and depends on the concentration of nanoparticulate drug and/or diluent in the liquid sample, as well as the droplet size produced by the spray-dryer nozzle. For deep lung delivery it is desirable for the collected product size to be less than about 2 μm in diameter; for delivery to the conducting airways it is desirable for the collected product size to be about 2 to about 6 μm in diameter, and for nasal delivery a collected product size of about 5 to about 100 μm is preferred. Collected products may then be used in conventional DPIs for pulmonary or nasal delivery, dispersed in propellants for use in pMDIs, or the particles may be reconstituted in water for use in nebulizers.

In some instances it may be desirable to add an inert carrier to the spray-dried material to improve the metering properties of the final product. This may especially be the case when the spray dried powder is very small (less than about 5 μm) or when the intended dose is extremely small, whereby dose metering becomes difficult. In general, such carrier particles (also known as bulking agents) are too large to be delivered to the lung and simply impact the mouth and throat and are swallowed. Such carriers typically consist of sugars such as lactose, mannitol, or trehalose. Other inert materials, including polysaccharides and cellulosics, may also be useful as carriers.

Spray-dried powders containing nanoparticulate drug particles may used in conventional DPIs, dispersed in propellants for use in pMDIs, or reconstituted in a liquid medium for use with nebulizers.

6. Freeze-Dried Nanoparticulate Compositions

For compounds that are denatured or destabilized by heat, such as compounds having a low melting point (i.e., about 70 to about 150° C.), or for example, biologics, sublimation is preferred over evaporation to obtain a dry powder nanoparticulate drug composition. This is because sublimation avoids the high process temperatures associated with spray-drying. In addition, sublimation, also known as freeze-drying or lyophilization, can increase the shelf stability of drug compounds, particularly for biological products. Freeze-dried particles can also be reconstituted and used in nebulizers. Aggregates of freeze-dried nanoparticulate drug particles can be blended with either dry powder intermediates or used alone in DPIs and pMDIs for either nasal or pulmonary delivery.

Sublimation involves freezing the product and subjecting the sample to strong vacuum conditions. This allows for the formed ice to be transformed directly from a solid state to a vapor state. Such a process is highly efficient and, therefore, provides greater yields than spray-drying. The resultant freeze-dried product contains drug and modifier(s). The drug is typically present in an aggregated state and can be used for inhalation alone (either pulmonary or nasal), in conjunction with diluent materials (lactose, mannitol, etc.), in DPIs or pMDIs, or reconstituted for use in a nebulizer.

C. Methods of Using Nanoparticulate Drug Aerosol Formulations

The aerosols of the present invention, both aqueous and dry powder, are particularly useful in the treatment of respiratory-related illnesses such as asthma, emphysema, respiratory distress syndrome, chronic bronchitis, cystic fibrosis, chronic obstructive pulmonary disease, organ-transplant rejection, tuberculosis and other infections of the lung, fungal infections, respiratory illness associated with acquired immune deficiency syndrome, oncology, and systemic administration of an anti-emetic, analgesic, cardiovascular agent, etc. The formulations and method result in improved lung and nasal surface area coverage by the administered drug.

In addition, the aerosols of the invention, both aqueous and dry powder, can be used in a method for diagnostic imaging. Such a method comprises administering to the body of a test subject in need of a diagnostic image an effective contrast-producing amount of the nanoparticulate aerosol diagnostic image contrast composition. Thereafter, at least a portion of the body containing the administered contrast agent is exposed to x-rays or a magnetic field to produce an x-ray or magnetic resonance image pattern corresponding to the presence of the contrast agent. The image pattern can then be visualized.

D. Summary of Advantages of the Compositions and Methods of the Invention

Using the compositions of the invention, essentially water-insoluble drugs can be delivered to the deep lung. This is either not possible or extremely difficult using aerosol formulations of micronized water-insoluble drugs. Deep lung delivery is necessary for drugs that are intended for systemic administration, because deep lung delivery allows rapid absorption of the drug into the bloodstream via the alveoli, thus enabling rapid onset of action.

The present invention increases the number of drug particles per unit dose and results in distribution of the nanoparticulate drug particles over a larger physiological surface area as compared to the same quantity of delivered micronized drug. For systemic delivery via the pulmonary route, this approach takes maximum advantage of the extensive surface area presented in the alveolar region—thus producing more favorable drug delivery profiles, such as a more complete absorption and rapid onset of action.

Moreover, in contrast to micronized aqueous aerosol dispersions, aqueous dispersions of water-insoluble nanoparticulate drugs can be nebulized ultrasonically. Micronized drug is too large to be delivered efficiently via an ultrasonic nebulizer.

Droplet size determines in vivo deposition of a drug, i.e., very small particles, about <2 microns, are delivered to the alveoli; larger particles, about 2 to about 10 microns, are delivered to the bronchiole region; and for nasal delivery, particles of about 5 to about 100 microns are preferred. Thus, the ability to obtain very small drug particle sizes which can "fit" in a range of droplet sizes allows more effective and more efficient (i.e., dose uniformity) targeting to the desired delivery region. This is not possible using micronized drug, as the particle size of such drugs is too large to target areas such as the alveolar region of the lung. Moreover, even when micronized drug is incorporated into larger droplet sizes, the resultant aerosol formulation is heterogeneous (i.e., not all droplets contain drug), and does not result in such the rapid and efficient drug delivery enabled by the nanoparticulate aerosol formulations of the invention.

The present invention also enables the aqueous aerosol delivery of high doses of drug in an extremely short time period, i.e., 1-2 seconds (1 puff). This is in contrast to the conventional 4-20 min. administration period observed with pulmonary aerosol formulations of micronized drug.

Furthermore, the dry aerosol nanoparticulate powders of the present invention are spherical and can be made smaller than micronized material, thereby producing aerosol compositions having better flow and dispersion properties, and capable of being delivered to the deep lung.

Finally, the aerosol compositions of the present invention enable rapid nasal delivery. Nasal delivery of such aerosol compositions will be absorbed more rapidly and completely than micronized aerosol compositions before being cleared by the mucociliary mechanism.

Drug Particles

The nanoparticles of the invention comprise a therapeutic or diagnostic agent, which in the invention are collectively are referred to as a "drug." A therapeutic agent can be a pharmaceutical, including biologics such as proteins and peptides, and a diagnostic agent is typically a contrast agent, such as an x-ray contrast agent, or any other type of diagnostic material. The drug exists as a discrete, crystalline phase. The crystalline phase differs from a non-crystalline or amorphous phase which results from precipitation techniques, such as those described in EPO 275,796.

The invention can be practiced with a wide variety of drugs. The drug is preferably present in an essentially pure form, is poorly soluble, and is dispersible in at least one liquid medium. By "poorly soluble" it is meant that the drug has a solubility in the liquid dispersion medium of less than about 10 mg/mL, and preferably of less than about 1 mg/mL.

Suitable drugs include those intended for pulmonary or intranasal delivery. Pulmonary and intranasal delivery are particularly useful for the delivery of proteins and polypeptides which are difficult to deliver by other routes of administration. Such pulmonary or intranasal delivery is effective both for systemic delivery and for localized delivery to treat diseases of the air cavities.

Preferable drug classes include proteins, peptides, bronchodilators, corticosteroids, elastase inhibitors, analgesics, anti-fungals, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, and respiratory illness therapies associated with acquired immune deficiency syndrome, oncology therapies, systemic administration of anti-emetics, analgesics, cardiovascular agents, etc.

The drug can be selected from a variety of known classes of drugs, including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

A description of these classes of drugs and a listing of species within each class can be found in Martindale, *The Extra Pharmacopoeia*, Twenty-ninth Edition (The Pharmaceutical Press, London, 1989), specifically incorporated by reference. The drugs are commercially available and/or can be prepared by techniques known in the art.

Preferred contrast agents are taught in the '684 patent, which is specifically incorporated by reference. Suitable diagnostic agents are also disclosed in U.S. Pat. No. 5,260,478; U.S. Pat. No. 5,264,610; U.S. Pat. No. 5,322,679; and U.S. Pat. No. 5,300,739, all specifically incorporated by reference.

Surface Modifiers

Suitable surface modifiers can preferably be selected from known organic and inorganic pharmaceutical excipients. Such excipients include various polymers, low molecular weight oligomers, natural products, and surfactants. Preferred surface modifiers include nonionic and ionic surfactants. Two or more surface modifiers can be used in combination.

Representative examples of surface modifiers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20° and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Tyloxapol is a particularly preferred surface modifier for the pulmonary or intranasal delivery of steroids, even more so for nebulization therapies.

Most of these surface modifiers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 1986), specifically incorporated by reference. The surface modifiers are commercially available and/or can be prepared by techniques known in the art.

Ratios

The relative amount of drug and surface modifier can vary widely and the optimal amount of the surface modifier can depend upon, for example, the particular drug and surface modifier selected, the critical micelle concentration of the surface modifier if it forms micelles, the hydrophilic-lipophilic-balance (HLB) of the surface modifier, the melting point of the surface modifier, the water solubility of the surface modifier and/or drug, the surface tension of water solutions of the surface modifier, etc.

In the present invention, the optimal ratio of drug to surface modifier is about 1% to about 99% drug, more preferably about 30% to about 90% drug.

The following examples are given to illustrate the present invention. It should be understood, however, that the invention is not to be limited to the specific conditions or details described in these examples.

Example 1

The purpose of this example was to demonstrate the ability to aerosolize a concentrated nanoparticulate dispersion in an ultrasonic nebulizer which incorporates a fine mesh screen in its design. An additional purpose of this example was to demonstrate that a therapeutic quantity of a concentrated nanoparticulate corticosteroid can be aerosolized in a very short period of time; e.g., two seconds or less.

Two different nanoparticulate dispersions of beclomethasone dipropionate (BDP) (1.25% and 10% BDP) were aerosolized using an ultrasonic nebulizer (Omron NE-U03 MicroAir®). The nebulizer generated droplets on a piezoelectric crystal and extruded them through a screen which contains ultrafine laser-drilled holes, producing an aerosol which has a very narrow particle size distribution in the range of approximately 1-5 μm. The device was connected to an Andersen cascade impactor with a flow rate at 28.3 liters per minute. For each formulation, the nebulizer was actuated for two seconds using a programmable timer. The actuation time roughly corresponds to one inhalation cycle with a pMDI. After actuation, each stage of the impactor was analyzed for drug deposition by HPLC analysis.

The data indicate that substantial quantities of drug substance were found on stages 3-6 of the cascade impactor, corresponding to aerodynamic droplet sizes of about 0.7 to 4.7 µm. The total amount of drug in the respirable droplet size range for deep lung delivery (i.e., particles less than about 2 microns; Stages 5, 6, and 7) was 11.72 µg for the 1.25% BDP (w/w) dispersion and 18.36 µg for the 10% BDP (w/w) dispersion. The total amount of drug in the respirable droplet size range for upper pulmonary delivery (i.e. particles about 2 to 5 microns; Stages 2, 3, 4, and 5) was 17.26 µg for the 1.25% BDP dispersion and 178.40 µg for the 10% BDP dispersion.

One advantage provided by nanoparticulate formulations is that the drug particles are small enough to pass through the finer mesh channels of the nebulizer. In contrast, conventional micronized drug material would be expected to clog the orifices in the screen. Cascade impactor data from an in vitro deposition study of a nanoparticulate BDP dispersion aerosolized by an Omron NE-U03 Ultrasonic Nebulizer are summarized in Table I below:

TABLE I

Observed In-Vitro Deposition Pattern of an Aerosolized Nanoparticulate BDP Dispersion

| Deposition Site/ Impactor Area | Droplet Size Range (µm)[a] | 1.25% BDP[b] (µg Collected) | 10% BDP[c] (µg Collected) |
| --- | --- | --- | --- |
| Stage 0 | 9.0-10.0 | 4.76 | 19.30 |
| Stage 1 | 5.8-9.0 | 1.95 | 37.50 |
| Stage 2 | 4.7-5.8 | 0.75 | 42.00 |
| Stage 3 | 3.3-4.7 | 1.73 | 79.40 |
| Stage 4 | 2.1-3.3 | 5.97 | 45.20 |
| Stage 5 | 1.1-2.1 | 8.81 | 11.80 |
| Stage 6 | 0.7-1.1 | 2.09 | 3.59 |
| Stage 7 | 0.4-0.7 | 0.82 | 2.97 |
| After Filter | <0.4 | 2.25 | 18.70 |
|  | TOTAL | 29.13 | 260.46 |
| Collar | N/A | 0.00 | N/A |
| Induction Port | N/A | 4.10 | 22.40 |
| Adapter | N/A | N/A | N/A |
| Tube | N/A | N/A | 10.98 |

[a] All results based on 2 second actuation with the Omron NE-U03.
[b] Particle Size of concentrate BDP 1.25% (w/w): mean of 171 nm, 90% < 234 nm, standard deviation 30 nm
[c] Particle Size of concentrate BDP 10% (w/w): mean of 94 nm, 90% < 130 nm, standard deviation 30 nm The results, which are graphically depicted in FIG. 1, show substantial deposition of drug at Stages 2, 3, 4, and 5. This corresponds to delivery to conducting airways. Most of the drug substance is found in droplets of about 2 to about 6 µm, which are ideal for delivery to the bronchiole region.

Example 2

The purpose of this example was to demonstrate aerosolization of a nanoparticulate dispersion using a using a jet nebulizer (Circulaire®, Westmed, Inc., Tucson, Ariz.), which can produce aqueous droplets in the size range of 0.5-2.0 µm. Such droplet sizes are suitable for delivery to the alveolar region of the lung, i.e., deep lung delivery.

A nanoparticulate dispersion of BDP was prepared by wet milling micronized drug substance in an aqueous tyloxapol surface modifier solution until a satisfactory particle size distribution had been obtained. The formulation was evaluated by light scattering methods (Microtrac UPA, Leeds & Northrup) and was found to have a mean particle size of 139 nm, with 90% of the particles being less than 220 nm (volume statistics).

The delivery performance of the BDP/surface modifier dispersion in a jet nebulizer was evaluated as follows: Approximately 3.5 ml of the BDP/surface modifier dispersion (2 mg/ml) was added to the nebulizer bowl, and the nebulizer mouthpiece was connected to the throat of a cascade impactor apparatus with an airtight seal. The nebulizer and cascade impactor were then operated under suitable pressure and flow conditions for approximately 4 minutes using a 4 seconds on/4 seconds off cycle. Upon completion of the nebulization, each section of the apparatus was rinsed with acetonitrile and the washings diluted volumetrically.

The quantity of drug substance present in each section of the apparatus was determined by high performance liquid chromatography.

Results

Figure 2:
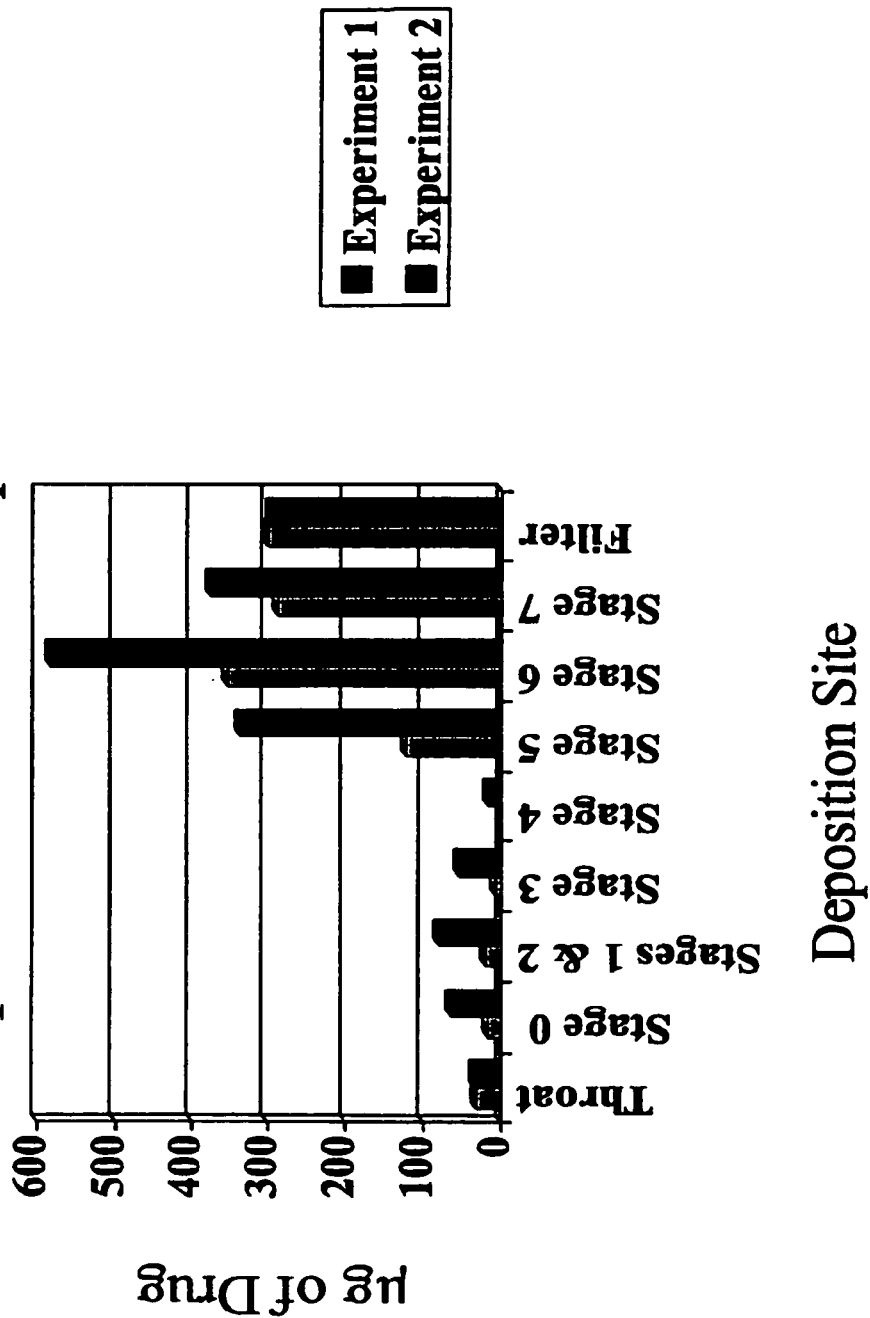
FIG. 2: Shows an in vitro deposition pattern of a concentrated aerosolized beclomethasone dipropionate dispersion from a jet nebulizer.

Analysis of the chromatograms showed that relatively little drug substance was deposited in the higher regions of the cascade impactor apparatus, while substantial quantities of material appeared on stages 5-7, as well as on the exit filter. In Experiment 1, approximately 92% of the emitted dose (ex-device) was contained in droplets<2.1 µm in diameter; in Experiment 2 the value was 86%. The results indicate that substantial quantities of drug substance were found on cascade impactor stages 5, 6, and 7, corresponding to droplet sizes of about 0.43 to about 2.1 microns. The smallest drug particle size normally accessible by conventional micronization methods for raw materials is about 2 to 3 microns, which is clearly larger than the droplets generated by this jet nebulizer. Detailed results of the cascade impactor study are presented Table II below, and graphically in FIG. 2.

TABLE II

Observed In Vitro Deposition Pattern of a Nanoparticulate BDP Suspension

| Deposition Site | Droplet Size Range (µm) | Experiment 1[a] | Experiment 2[a] |
| --- | --- | --- | --- |
| Throat |  | 33.13 | 36.00 |
| Preselector, Stage 0 | >9.0 | 17.64 | 65.27 |
| Stages 1 and 2 | 4.7-9.0 | 19.90 | 80.69 |
| Stage 3 | 3.3-4.7 | 8.76 | 55.59 |
| Stage 4 | 2.1-3.3 | 2.13 | 17.90 |
| Stage 5 | 1.1-2.1 | 122.41 | 336.16 |
| Stage 6 | 0.65-1.1 | 354.20 | 580.20 |
| Stage 7 | 0.43-0.65 | 286.42 | 376.11 |
| filter | <0.43 | 297.60 | 297.15 |
| TOTAL |  | 1142.19 | 1845.07 |

[a] µg of BDP Collected

In contrast to Example 1, which used an ultrasonic nebulizer (Omron NE U03 MicroAir®) that generates droplets in the range of 2-6 µm, this example used a jet nebulizer that generates droplets in the range of <2 µm. The successful deposition of aerosol drug particles at Stages 6 and 7 demonstrates the effectiveness of using such compositions for deep lung delivery.

Example 3

The purpose of this example was to demonstrate the preparation of a nanoparticulate dry powder for use in a DPI.

40.0% (w/w) naproxen, 4.00% (w/w) PVP K29/30 (a surface modifier), and 56.0% (w/w) deionized water were milled with 500 µm SDy-20 polymeric media for 7.5 hours to achieve a mean particle size of 254 nm, with 90% of the particles having a size of less than 335 nm. The material was diluted to 20% (w/w) naproxen and further milled with 50 µm SDy-20 media for a period of 6 hours to yield a mean particle size of 155 nm, with 90% of the particles having a particle size of less than 212 nm. The nanoparticulate dispersion was then diluted to 2% (w/w) naproxen with sufficient quantities of Sterile Water for Injection. The suspension was then spray-dried using a Yamato GB-22 operating with the following parameters:

| | |
|---|---|
| Inlet Temp.: | 130° C. |
| Outlet Temp.: | 71-76° C. |
| Drying Air: | 0.37 m³/min. |
| Atom. Air: | 2 M Pa |
| Pump Speed: | ca. 8.4 mL/min. |

Figure 3:
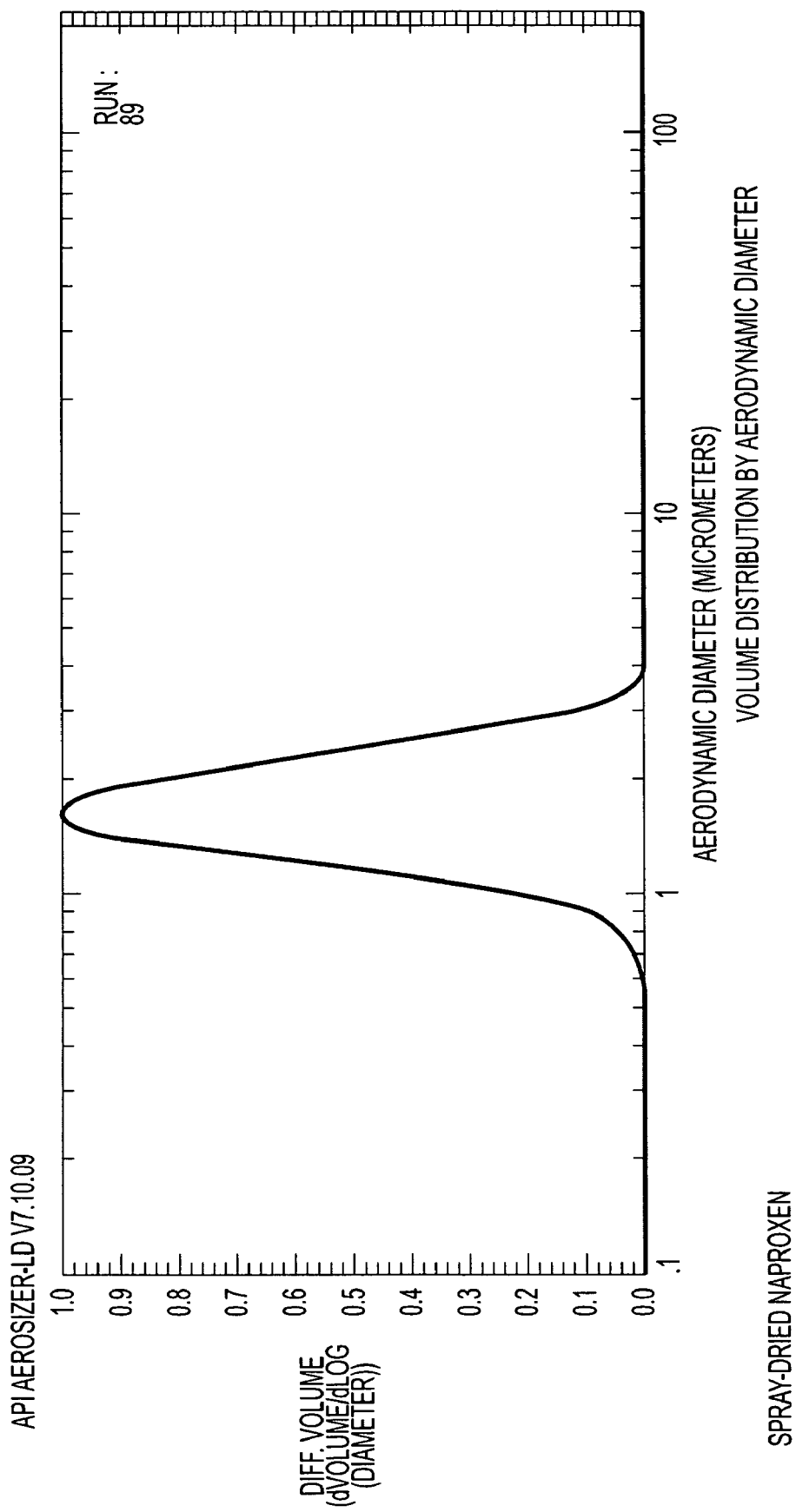
FIG. 3: Shows the aerodynamic volume distribution diameter of a spray-dried naproxen aerosol (2% (w/w) naproxen).

The resultant nanoparticulate powder possessed a MMAD of 1.67 µm, with 90% of the particles having a MMAD of less than 2.43 µm, as determined by a time-of-flight particle sizing instrument. See FIG. 3, which shows the volume distribution by the aerodynamic diameter of the spray-dried naproxen aerosol. Thus, all particles fell within the respirable size range required for pulmonary deposition. Additionally, greater than 50 percent of the particle population fell within the size required for peripheral lung deposition (alveolar, <2 µm).

Figure 4:
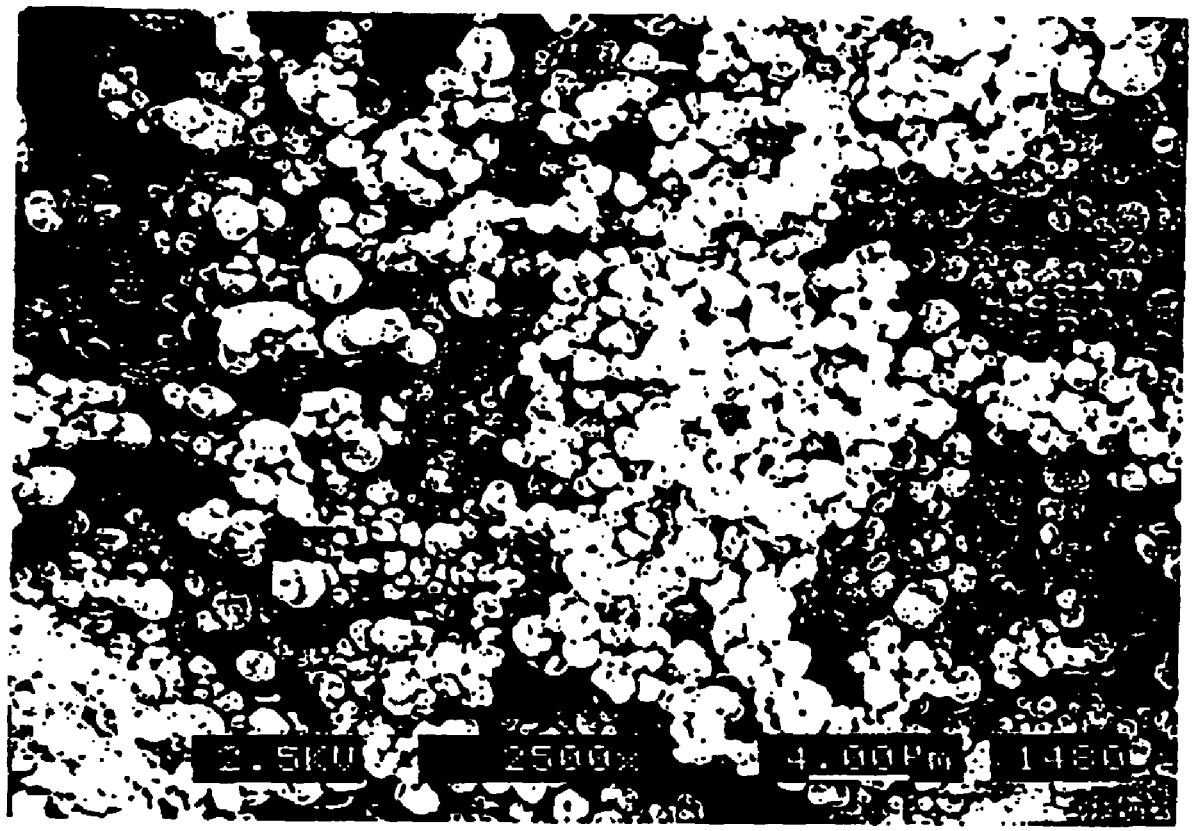
FIG. 4: Shows a scanning electron micrograph of spray-dried naproxen aerosol particles (aggregated naproxen/polyvinylpyrrolidone (surface modifier) nanoparticles, demonstrating the overall uniformity of size and the spherical nature of the particles.

Interestingly, the spray-dried drug particles also demonstrated a spherical shape, which will improve the flow properties of the powder (as compared to prior micronized spray-dried powder formulations). The electron micrograph of FIG. 4 clearly shows the overall uniformity of size and the spherical nature of the particles. In addition, the exterior surface of the drug particle, which is composed of the polymeric stabilizer, may have advantages in limiting moisture uptake upon storage.

Lastly, to demonstrate that these spray-dried particles are constructed of aggregates of the original nanoparticulate drug, reconstitution in a liquid medium resulted in the return to the original nanoparticulate dispersion, with a mean particle size of 184 nm, and 90% of the particles having a size of less than 255 nm.

Example 4

The purpose of this example was to further demonstrate the ability to influence the aerodynamic size of the spray-dried nanoparticulate composition by using a different concentration of nanoparticulate drug dispersion.

The concentration of naproxen and surface modifier (PVP K29/30) was the same as in Example 5, except that the composition was diluted with Sterile Water for Injection to achieve a 5% (w/w) naproxen suspension. The spray-drier used was the Yamato GB-22, with the same operating parameters used in Example 4.

Figure 5:
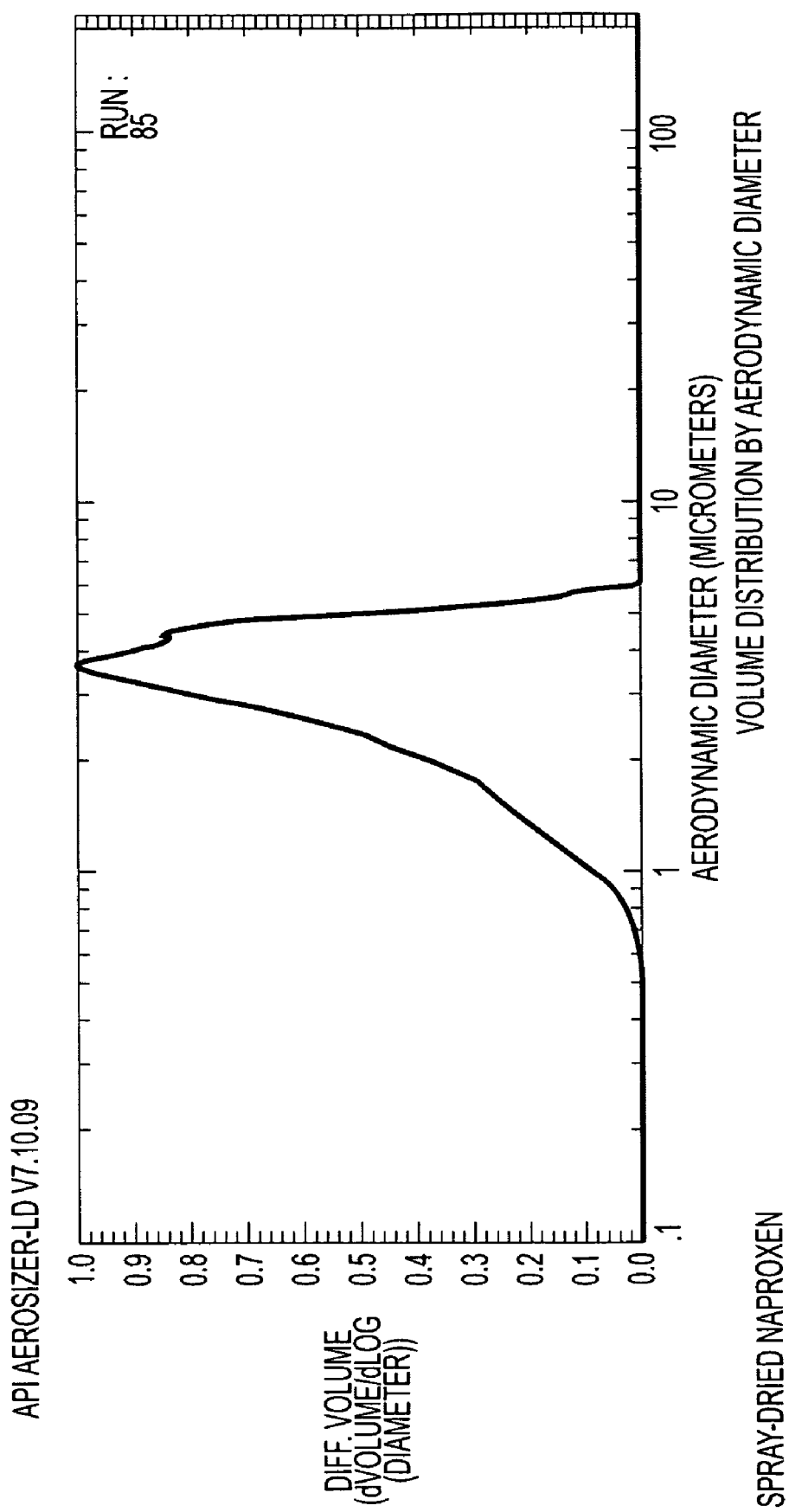
FIG. 5: Shows the aerodynamic volume distribution diameter of a spray-dried naproxen aerosol (5% (w/w) naproxen).

The resultant powder was composed of nanoparticulate aggregates with a MMAD of 2.91 µm, with 90% of the drug particles having a MMAD of less than 4.65 µm. This material is within the desired range for inhaled pulmonary deposition and may be more suitable for central airway targeting, i.e., within a range of 2 to 6 µm. See FIG. 5, which shows the volume distribution by the aerodynamic diameter of the spray-dried naproxen aerosol.

Example 5

The purpose of this example was to produce a spray-dried nanoparticulate powder for aerosol administration.

20.0% (w/w) triamcinolone acetonide (TA), 2.00% (w/w) HPC-SL (a surface modifier), 0.01% (w/w) benzalkonium chloride (BKC), and 76.9% (w/w) deionized water were milled in the presence of 500 µm SDy-20 polymeric media for approximately one hour. The final drug mean particle size was 169 nm, with 90% of the drug particles having a size of less than 259 nm. The nanoparticulate drug dispersion was then diluted to 10% (w/w) TA with a 0.01% BKC solution. The dispersion was then spray-dried using a Buchi B-191 spray-drier at the following settings:

| | |
|---|---|
| Inlet Temp.: | 130° C. |
| Outlet Temp. | 76° C. |
| Aspirator setting: | 90% capacity |
| Product feed: | 18% capacity |

Figure 6:
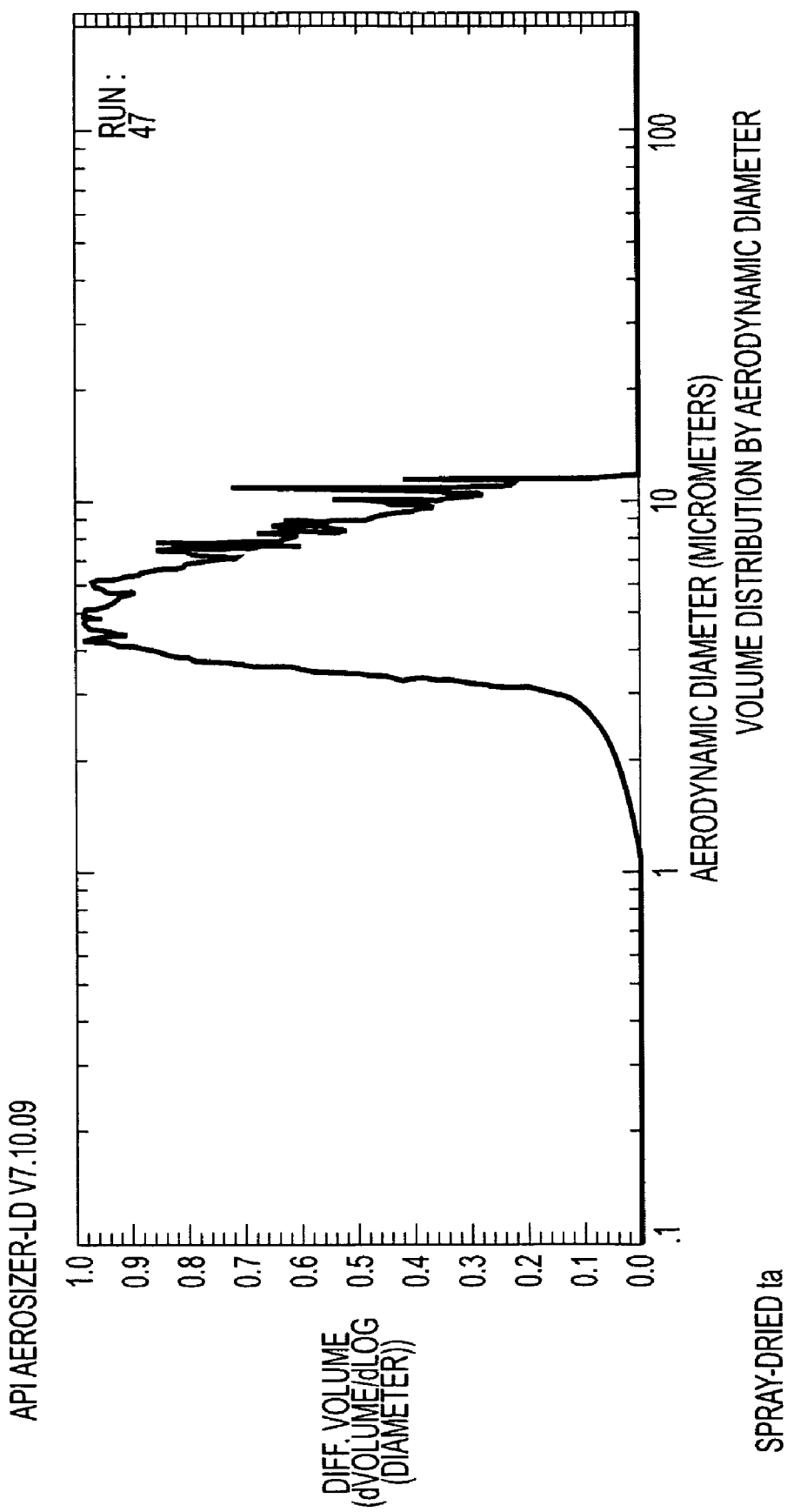
FIG. 6: Shows the aerodynamic volume distribution diameter of a spray-dried triamcinolone acetonide (TA) aerosol (10% (w/w) TA).

The resultant nanoparticulate powder possessed aggregates of nanoparticulate TA particles with a MMAD of 5.54 µm, and 90% of the TA particles had a MMAD of less than 9.08 µm via a time-of-flight measuring system. Thus, 50 percent of the particles fall within the respirable range for central airway (bronchiole deposition). See FIG. 6, which shows the volume distribution by the aerodynamic diameter of the spray-dried TA aerosol. In addition, the TA powder was of spherical shape as compared to the jet-milled drug, thus affording improved flow properties. Lastly, the powder redisperses in liquid medium to achieve well-dispersed nanoparticles of drug at a mean particle size of 182 nm.

Example 6

The purpose of this example was to produce a spray-dried nanoparticulate drug/surface modifier powder for aerosol administration, wherein the composition lacks a diluent. In addition, this example compares the deposition of the nanoparticulate powder with the deposition of a micronized drug substance in a dry-powder delivery device. 10% (w/w) budesonide, 1.6% (w/w) HPMC (surface modifier), and 88.4% (w/w) deionized water were milled in the presence of 500 µm SDy-20 polymeric media for 1.5 hours. The resultant mean particle size was 166 nm, with 90% of the particles having a size of less than 233 nm. The nanoparticulate dispersion was then diluted to 0.5% (w/w) budesonide with deionized water. The dispersion was spray-dried using a Yamato GB-22 spray-dryer operating at the following parameters:

| | |
|---|---|
| Inlet Temperature: | 125° C. |
| Drying Air: | 0.40 m³/minute |
| Atomizing Air: | 0.2 MPa |
| Outlet Temperature: | 60-61° C. |

The resultant nanoparticulate aggregates possessed a MMAD of 1.35 µm, with 90% of the particles having a MMAD of less than 2.24 µm, as measured by time-of-flight methodology.

A final powder blend was made, composed of 4% (w/w) nanoparticulate budesonide/surface modifier (3.2% (w/w) drug) and 96% lactose. The mixing was carried out using a Patterson-Kelley V-Blender with Lexan shell. The same procedure was followed for micronized budesonide at 3.4% (w/w) drug (Sicor, Via Terrazano 77, Italy).

Each drug powder—the nanoparticulate and the micronized—was then loaded into a Clickhaler™ (ML Laboratories plc, England), having a 1.5 mm³ dosing chamber. Each unit was evaluated using an Andersen cascade impactor operating at approximately 60 liters per minute. Five actuations were delivered to the impactor and the unit was then disassembled and the collection plates analyzed via HPLC. This was performed in triplicate. The data as percent of emitted dose from the DPI is shown below in Table III.

TABLE III

In vitro Deposition of Nanoparticulate Budesonide
vs Micronized Budesonide in a DPI[a]

| Impactor Region | Aerodynamic Particle Size Range (μm) | Nanoparticulate Budesonide | Micronized Budesonide |
|---|---|---|---|
| Stage 0 | 5.9-10.0 | 14.1 | 16.7 |
| Stage 1 | 4.1-5.9 | 1.03 | 5.31 |
| Stage 2 | 3.2-4.1 | 3.09 | 4.76 |
| Stage 3 | 2.1-3.2 | 14.9 | 7.74 |
| Stage 4 | 1.4-2.1 | 26.7 | 5.73 |
| Stage 5 | 0.62-1.4 | 12.1 | 3.48 |
| Stage 6 | 0.35-0.62 | 2.22 | N/D |
| Stage 7 | 0.15-0.35 | 0.39 | N/D |
| After Filter | <0.15 | N/D | N/D |
| Total Respirable | <5.9 | 60.4 | 27.0 |
| Total Systemic | <2.1 | 41.4 | 9.21 |
| Cone | N/A | 0.40 | 0.94 |
| Induction Port | N/A | 12.7 | 44.0 |
| Adapter | N/A | 12.4 | 11.3 |

[a]As percent of emitted dose through device. Cascade Impactor operated at ca. 60 L/min.

The results indicate that the nanoparticulate budesonide powder delivered 60.4% of the dose to the respirable regions of the impactor, while only 27% of the micronized drug was delivered to the same region. Furthermore, 41.4% of the nanoparticulate aggregates were found in the region corresponding to alveolar lung deposition, in contrast to only 9.21% for the micronized material. Thus, the spray-dried nanoparticulate aggregates were more efficiently aerosolized than the micronized drug. About 450% more in vitro deposition was observed within the systemic region for the nanoparticulate aggregates as compared to the micronized drug blend (measured as percent of delivered dose). Electron micrographs of the nanoparticulate and micronized dry substance formulations are shown in FIG. 7.

Example 7

The purpose of this example was to demonstrate the production of freeze-dried nanoparticulate drug compositions for use in aerosol formulations.

10.0% (w/w) of a novel anti-emetic, 2.00% (w/w) of Poloxamer 188® (a surface modifier), 0.500% (w/w) PVP C-15, and 87.5% (w) of Sterile Water for Injection was milled in the presence of 500 μm SDy-20 polymeric media for a period of 2 hours. A composition having a mean particle size of 286 nm, with 90% of the particles having a size of less than 372 nm, was determined via the Horiba LA-910 particle sizer. This material was then diluted to 5% (w/w) drug with Sterile Water for Injection and subjected to 60 minutes milling with 50 μm SDy-20 media. The final particle size obtained was 157 nm, with 90% of the drug particles having a size of less than 267 nm, as determined via the Horiba LA-910. This dispersion was then utilized in a series of freeze-drying experiments below.

The freeze-dryer utilized was an FTS Dura-Stop system with operating parameters as follows:

| Product freeze temperature: −30° C. (2 hours hold) | |
|---|---|
| Primary Drying: | |
| 1. Shelf temperature set: | −25° C. |
| Chamber vacuum: | 100 mT |
| Hold time: | 2000 min. |

| Product freeze temperature: −30° C. (2 hours hold) | |
|---|---|
| Primary Drying: | |
| 2. Shelf temp.: | −10° C. |
| Chamber vacuum: | 100 mT |
| Hold time: | 300 min. |
| 3. Shelf temp.: | 0° C. |
| Chamber vacuum: | 100 mT |
| Hold time: | 300 min. |
| 4. Shelf temp.: | 20° C. |
| Chamber vacuum: | 50 mT |
| Hold time: | 800 min. |

Example 7A

The following freeze-dried material was reconstituted in deionized water and examined for particle size distribution via the Horiba LA-910 particle analyzer: 5.00% (w/w) novel anti-emetic, 5.00% (w/w) dextrose, 1.00% (w/w) Poloxamer 188®, 0.250% (w/w) PVP C-15, and 88.8% (w/w) Sterile Water for Injection.

Figure 8:
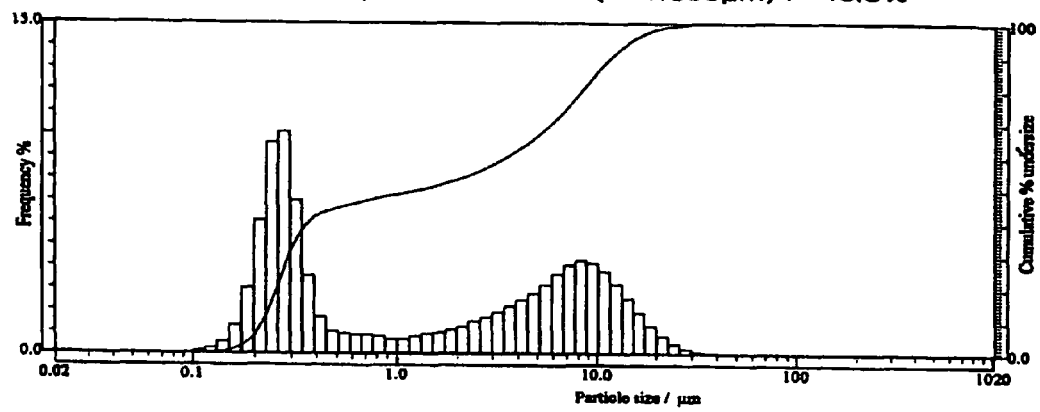
FIG. 8: Shows the particle size distribution (by volume) of a reconstituted freeze-dried anti-emetic aerosol containing dextrose diluent.

The average particle size of the reconstituted nanoparticulate dispersion was 4.23 μm, with 90% of the particles having an average particle size of less than 11.8 μm. The resultant material demonstrates that aggregates were present in the freeze-dried material having suitable particle sizes for pulmonary deposition. See FIG. 8, which shows the particle size distribution of the freeze-dried anti-emetic aerosol. (For this example, the particle sizes were measured by weight.)

Example 7B

The following freeze-dried material was reconstituted in deionized water and examined for particle size distribution via the Horiba LA-910 particle analyzer: 1.00% (w/w) novel anti-emetic, 5.00% (w/w) mannitol, 0.200% (w/w) Poloxamer 188, 0.050% (w/w) PVP C-15, and 93.8% (w/w) Sterile Water for Injection.

Figure 9:
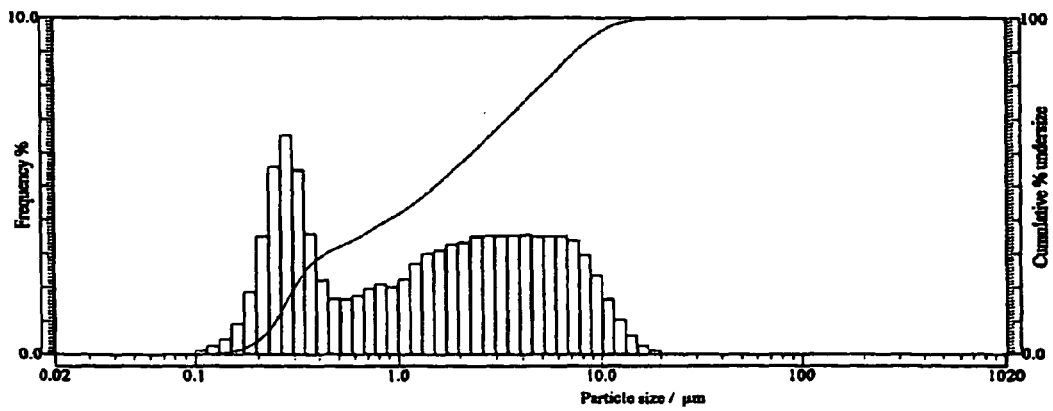
FIG. 9: Shows the particle size distribution of a reconstituted freeze-dried anti-emetic aerosol containing mannitol diluent.

The resultant powder when reconstituted demonstrated an average particle size of 2.77 μm, with 90% of the drug particles having an average particle size of less than 7.39 μm. Thus, aggregates of the nanoparticulate anti-emetic have a particle size within an acceptable range for pulmonary deposition after patient inhalation. See FIG. 9, which shows the particle size distribution of the freeze-dried anti-emetic aerosol. Also, if larger aggregates are generated (beyond about 5 to about 10 μm), jet-milling may be employed to decrease the particle size distribution of the system for pulmonary indications.

All of the dry powder inhalation systems can be utilized in either unit dose or multi-dose delivery devices, in either DPIs or pMDIs, and in nebulizer systems.

Example 8

The purpose of this prophetic example is to demonstrate the production of a propellant-based pMDI. This aerosol dosage form for pulmonary deposition has been the most routinely prescribed for asthma indications. The system is pressurized by using a propellant, such as a CFC or HFA (hydrofluorinated alkane), which functions as the delivery medium for a micronized drug. Additionally, a valve lubricant is present. These are typically the only components for suspension-based pMDIs. The micronized drug is jet-milled to the appropriate size for lung deposition (about 3 to about 5 μm).

In contrast, the present invention is directed to the use of either discrete nanoparticles or aggregates of nanoparticles. For preparation of discrete nanoparticulate drug, a non-aqueous milling medium is used, comprised of a high boiling point propellant. By employing a CFC-11 or trichloromonofluoromethane milling medium, nanoparticulate drug with suitable modifier can be made in a non-pressurized milling system. For example, the boiling point of CFC-11 is 23.7° C. (according to the Merck Index). Thus, by maintaining the milling chamber temperature below 23.7° C., the CFC-11 remains intact during the size reduction process without developing internal pressure.

After the size reduction process, the propellant can be evaporated and reclaimed in a condenser. The resultant powder of nanoparticulate drug and surface modifier can then be resuspended in non-CFC propellants. Compounds HFA-134a (tetrafluoroethane) and HFA-227 (heptafluoropropane) (Solvay Fluorides, Inc., Greenwich, Conn.; Dupont Fluorochemicals, Wilmington, Del.) are the most widely recognized non-CFC propellants. These can be pressure-filled into canisters containing the nanoparticulate drug and surface modifier.

Example 8A

The purpose of this example was to prepare a nanoparticulate aerosol formulation in a non-aqueous, non-pressurized milling system.

Figure 10:
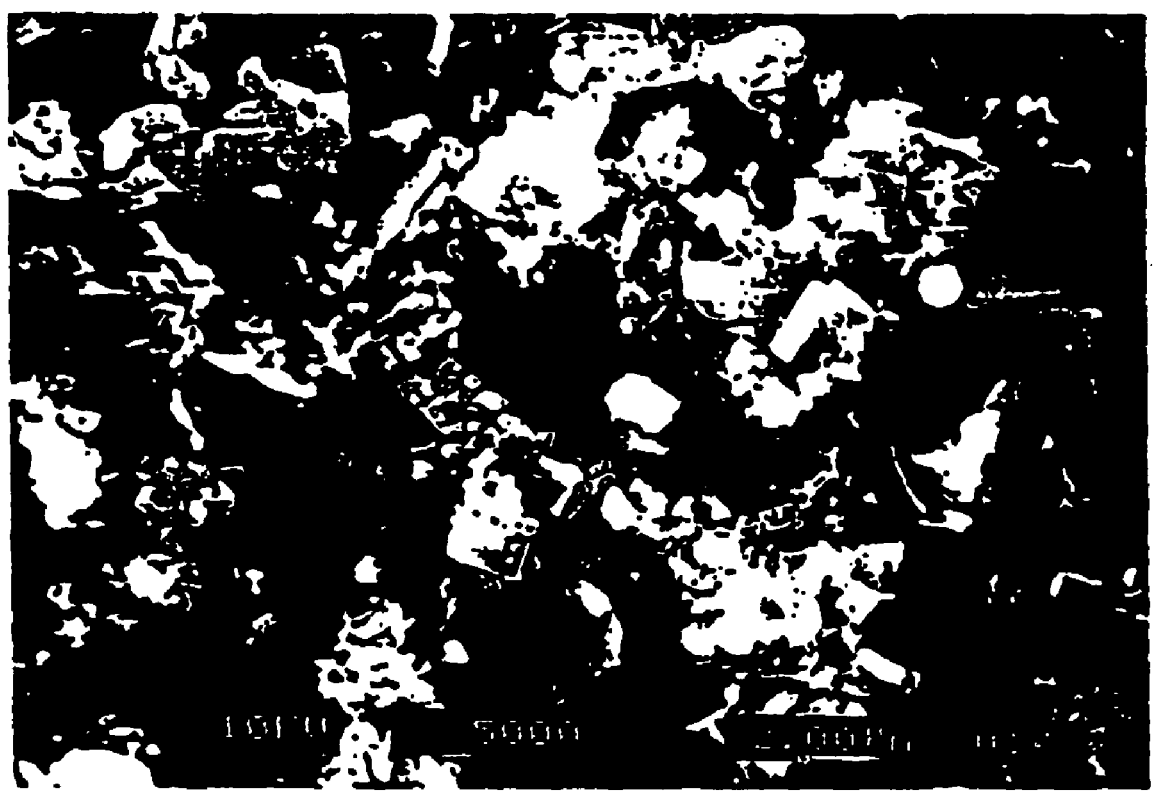
FIG. 10: Shows a scanning electron micrograph of nanoparticulate TA milled in a non-pressurized propellant system.
Figure 11:
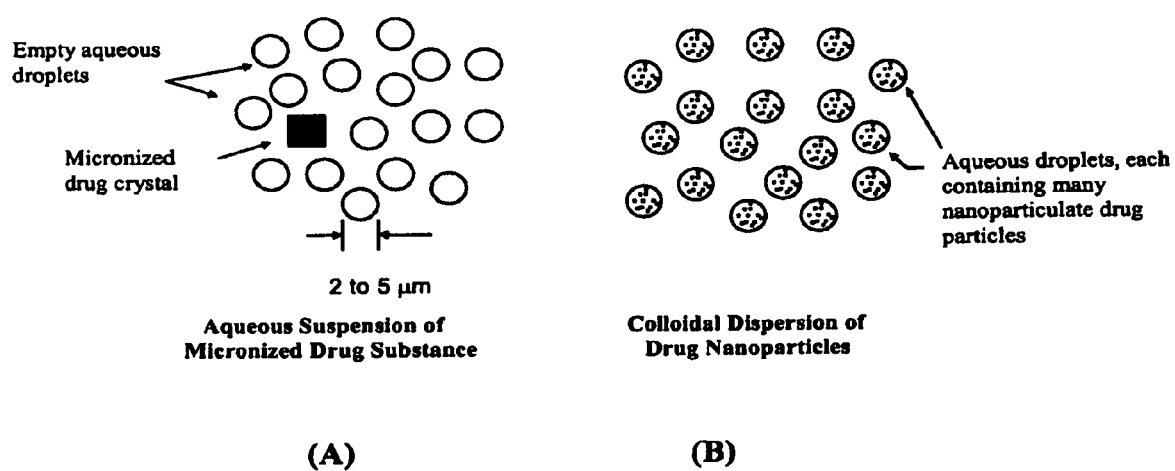
FIG. 11.

The following material was subjected to milling for 1.5 hrs with SDy-20 500 μm polymeric media: 5.00% (w/w) triamcinolone acetonide (TA), 0.500% (w/w) Span 85® (surface modifier), and 94.5% (w/w) CFC-11. The resultant dispersion was then harvested and the propellant evaporated. A scanning electron microgragh was taken of the resultant powder to inspect for size reduction of the drug crystals. See FIG. 10. Significant size reduction of drug particles was observed, and a large population of smaller drug crystals was found to be present. This material is of sufficient size to be respirable for inhaled administration via a pMDI or DPI system.

An exemplary corticosteroid formulation can comprise the following: 0.066% (w/w) nanoparticulate TA, 0.034% (w/w) Span 85, and 99.9% HFA-134a. Assuming a product density of 1.21 g/ml and a 50 μl metering valve, a theoretical delivery of 40 μg TA is achieved. If necessary, this quantity can be modified to compensate for actuator efficiency. Ideally, the nanoparticulate powder can be dispensed into an appropriate container, followed by pressurized propellant filling, or a bulk slurry can be prepared and introduced into the final form by cold filling or pressure filling.

Example 9

The purpose of this example was to describe the use of a nanoparticulate aerosol in a propellant system operating at pressurized conditions. A pressurized system allows the processing to progress at ambient room temperature.

The milling is conducted using either ball milling with ceramic/glass media or high-energy Dyno-milling with modifications to contain approximately 100 psig. The intent is to load the unit with chilled propellant and seal the sample ports. Thus, if the mill or roller bottle is at room temperature, the propellant will vaporize to maintain equilibrium within the containment system. A balance will be made between propellant in a liquid state and in a vapor state. This allows for milling in a liquid medium (the propellant) at temperatures above the propellant's boiling point.

Exemplary useful non-chlorinated propellants include HFA-134a (tetrafluoroethane), comprising about 50 to about 99.9% of final product weight, milling within pressure at/below 100 psig, and temperatures at/below 25° C.; and HFA-227 (heptafluoropropane), comprising about 50 to about 99.9% of final product weight, milling within pressure at/below 53 psig, and temperatures at/below 25° C. In addition, chlorinated propellants can be used in this embodiment. Exemplary chlorinated propellants include Freon-12 (dichlorodifluoromethane), comprising about 50 to about 99.9% of milling composition, processed within pressure at/below 85 psig, and temperatures at/below 25° C.; and Freon-114 (dichlorotetrafluoroethane), comprising about 50 to about 99.9% of milling slurry, processed at pressure at/below 19 psig, and temperatures at/below 250.

Example 9A

In this prophetic example, the following compounds can be combined for an exemplary budesonide aerosol composition to be used in a propellant system operating at pressurized conditions: 5.00% (w/w) budesonide, 0.500% PVP C-15, and 94.5% (w/w) HFA-134a.

The nanoparticulate aerosol composition would be further diluted as necessary to obtain desired delivery doses.

Example 9B

In this prophetic example, the following compounds can be combined for an exemplary TA aerosol composition to be used in a propellant system operating at pressurized conditions: 5.00% (w/w) TA, 0.500% PEG-400, and 94.5% (w/w) HFA-227.

The nanoparticulate aerosol composition would be further diluted as necessary to obtain desired delivery doses.

Example 10

The purpose of this example was to demonstrate the use of powders comprising spray-dried or freeze-dried nanoparticulate aggregates or discrete nanoparticulate particles in propellant systems for inhalation. The MMAD of the nanoparticulate aggregates would be about 0.5 μm to about 6.0 μm, and the mean particle diameter of the discrete nanoparticulate drug particles would be about <1000 nm. This allows for aqueous milling and subsequent water removal. The remaining powder can then be reconstituted with a propellant, such as those listed above.

The following can be combined for use in a propellant based system for inhalation: 0.704% (w/w) nanoparticulate agent/surface modifier and 99.3% (w/w) HFA-227. The resultant nanoparticulate powder is a spray-dried aggregate with a MMAD of 2.0 μm. Based on a theoretical product density of 1.42 g/ml and a metering valve of 100 μl, a dose of 1000 μg could be expected through-the-valve.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A method for making a propellant-based dry powder composition, comprising:
   (a) obtaining dry powder of a nanoparticulate drug composition; and then (b) dispersing the dry powder in at least one propellant,
wherein the nanoparticulate drug composition: (i) comprises a poorly soluble drug, (ii) has an effective average particle size of less than 1000 nm or equal to about 1000 nm, and (iii) has a surface modifier adsorbed on the surface of the drug particles, and
wherein step (a) comprises:
(i) forming an aqueous nanoparticulate dispersion of the drug and surface modifier; and
(ii) spray-drying or freeze-drying the nanoparticulate dispersion to form a dry powder of spherically shaped aggregates of the nanoparticulate drug and surface modifier, wherein the aggregates have a diameter of less than 100 microns or equal to about 100 microns.

2. The method of claim 1, further comprising adding a diluent to the nanoparticulate dispersion prior to spray-drying.

3. The method of claim 2, wherein the diluent is lactose or mannitol.

4. The method of claim 1, further comprising adding a diluent to the nanoparticulate dispersion prior to freeze-drying.

5. The method of claim 4, wherein the diluent is lactose or mannitol.

6. The method of claim 1, wherein the propellant is selected from the group consisting of a chlorinated propellant, a non-chlorinated propellant, a hydrofluorinated alkane, and a halogenated hydrocarbon propellant having a low boiling point.

7. The method of claim 1, wherein the drug is selected from the group consisting of proteins, peptides, elastase inhibitors, analgesics, a drug for treating cystic-fibrosis, a drug for treating asthma, a drug for treating emphysema, a drug for treating respiratory distress syndrome, a drug for treating chronic bronchitis, a drug for treating chronic obstructive pulmonary disease, a drug for treating organ-transplant rejection a drug for treating tuberculosis and other infections of the lung, a drug for treating fungal infection, a drug for treating respiratory illness caused by acquired immune deficiency syndrome, an oncology drug, an anti-emetic, a cardiovascular agent, beclomethasone dipropionate, naproxen, triamcinolone acetonide, budesonide, and an anti-emetic.

8. The method of claim 1, wherein the surface modifier is selected from the group consisting of a nonionic surfactant and an ionic surfactant.

9. The method of claim 1, wherein the surface modifier is selected from the group consisting of tyloxapol, cetyl pyridinium chloride, gelatin, casein, lecithin, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil, polyoxyethylene sorbitan fatty acid esters; polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl cellulose, hydroxypropyl methylcellulose, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers, poloxamines, a charged phospholipid, dioctylsulfosuccinate (DOSS), dialkylesters of sodium sulfosuccinic acid, sodium lauryl sulfate, alkyl aryl polyether, sulfonate, a mixture of sucrose stearate and sucrose distearate, p-isononylphenoxy-poly-(glycidol), $C_{18}H_{37}CH_2(CON(CH_3)—CH_2(CHOH)_4(CH_2OH)_2$, decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside.

* * * * *